United States Patent [19]
Chandrasekhar et al.

[11] Patent Number: 6,124,311

[45] Date of Patent: Sep. 26, 2000

[54] METHODS FOR TREATING RESISTANT TUMORS

[75] Inventors: Srinivasan Chandrasekhar, Indianapolis; Anne H. Dantzig, Crawfordsville; Robert L. Shepard, Noblesville; James J. Starling, Carmel; Mark A. Winter, Indianapolis, all of Ind.

[73] Assignee: Eli Lilly and Company, Indianapolis, Ind.

[21] Appl. No.: 08/674,771

[22] Filed: Jun. 28, 1996

Related U.S. Application Data

[63] Continuation-in-part of application No. 08/323,176, Oct. 14, 1994, abandoned.

[51] Int. Cl.[7] .......................... A61K 31/44; A61K 31/70; A61K 31/535; A61K 31/445; A61K 31/40; A61K 31/335; A61K 31/16

[52] U.S. Cl. .................. 514/283; 514/34; 514/232.5; 514/232.7; 514/324; 514/422; 514/449; 514/629

[58] Field of Search .................................... 514/283, 324, 514/34, 449, 629, 422, 237.5

[56] References Cited

U.S. PATENT DOCUMENTS

| | | |
|---|---|---|
| 4,133,814 | 1/1979 | Jones et al. . |
| 4,230,862 | 10/1980 | Suarez et al. . |
| 4,380,635 | 4/1983 | Peters . |
| 5,482,949 | 1/1996 | Black et al. . |

FOREIGN PATENT DOCUMENTS

| | | |
|---|---|---|
| 0 617 030 | 9/1994 | European Pat. Off. . |
| 0 652 004 | 5/1995 | European Pat. Off. . |
| 668 075 | 8/1995 | European Pat. Off. ....... A61K 31/00 |
| WO 95/17382 | 12/1993 | WIPO ........................... C07D 209/04 |
| WO 95/17095 | 6/1995 | WIPO ........................... A01N 43/38 |

OTHER PUBLICATIONS

Jones, et al., *J. Med. Chem.*, 27:1057–1066 (1984).
M. Lehnert, *J. Neuro–Oncology*, 22:239–243 (1994).
Osborne, et al., *J. Clinical Oncology*, 7(6):710–717 (1989).
Carter et al., Chemotherapy of Cancer, 2nd Ed, (1981) pp. 82 and 83.

*Primary Examiner*—Jerome D. Goldberg
*Attorney, Agent, or Firm*—Elizabeth A. Dawalt; Brian P. Barrett

[57] ABSTRACT

The present invention provides methods for reversing multidrug resistance in a resistant neoplasm by treating a mammal in need of said treatment with a substituted indole, benzofuran, benzothiophene, naphthalene, or dihydronaphthalene. This invention also provides methods for treating neoplasms in a mammal which comprises administering to a mammal in need of this treatment a substituted indole, benzofuran, benzothiophene, naphthalene, or dihydronaphthalene in combination with an oncolytic agent.

17 Claims, No Drawings

METHODS FOR TREATING RESISTANT TUMORS

CROSS-REFERENCE TO RELATED APPLICATION

This application is a continuation-in-part of U.S. patent application Ser. No. 08/323,176 filed Oct. 14, 1994, now abandoned.

BACKGROUND OF THE INVENTION

Along with surgery and radiotherapy, chemotherapy continues to be an effective therapy for many cancers. In fact, several types of cancer are now considered to be curable by chemotherapy and include Hodgkin's disease, large cell lymphoma, acute lymphocytic leukemia, testicular cancer and early stage breast cancer. Other cancers such as ovarian cancer, small cell lung and advanced breast cancer, while not yet curable, are exhibiting positive response to combination chemotherapy.

One of the most important unsolved problems in cancer treatment is drug resistance. Drug resistance is the name given to the circumstance when a disease does not respond to a treatment drug or drugs. Drug resistance can be either intrinsic, which means the disease has never been responsive to the drug or drugs, or it can be acquired, which means the disease ceases responding to a drug or drugs that the disease had previously been responsive to. Multidrug resistance is a specific type of drug resistance that is characterized by cross-resistance of a disease to more than one functionally and/or structurally unrelated drugs. Multidrug resistance in the field of cancer, is discussed in greater detail in "Detoxification Mechanisms and Tumor Cell Resistance to Anticancer Drugs," by Kuzmich and Tew, particularly section VII "The Multidrug-Resistant Phenotype (MDR)," *Medical Research Reviews*, Vol. 11, No. 2, 185–217, (Section VII is at pp. 208–213) (1991); and in "Multidrug Resistance and Chemosensitization: Therapeutic Implications for Cancer Chemotherapy," by Georges, Sharom and Ling, *Advances in Pharmacology*, Vol. 21, 185–220 (1990).

The drug resistance problem is a reason for the added importance of combination chemotherapy, as the therapy both has to avoid the emergence of resistant cells and to kill pre-existing cells which are already drug resistant.

Anthracyclines represent an important class of oncolytic agents. Doxorubicin, an anthracycline, which is also known in the art as ADRIAMYCIN™, is a drug of choice in the clinical management of breast cancer. Therapy with anthracyclines such as doxorubicin is complicated by the appearance of the anthracycline resistant phenotype which limits or negates the oncolytic activity of doxorubicin.

Taxol® (paclitaxel) is an antineoplastic taxane derivative originally isolated from Taxus spp. yew tree. This compound, and later derivatives thereof, are useful in the treatment of metastatic ovarian carcinoma which is refractory to first-line chemotherapy.

Topoisomerase inhibitors represent a further class of oncolytic agents. Epipodophyllotoxins such as ETOPOSIDE® and TENIPOSIDE® are topoisomerase inhibitors which are useful in the therapy of neoplasms of the testis, small-cell lung and other lung, breast, Hodgkin's disease, non-Hodgkin's lymphomas, acute granulocytic leukemia and Karposi's sarcoma. The therapeutic utility of the epipodophyllotoxins is limited by the appearance of the epipodophyllotoxin resistant phenotype.

One form of multi-drug resistance (MDR) is mediated by a membrane bound 170–180 kD energy-dependent efflux pump designated as P-glycoprotein (P-gp). P-glycoprotein has been shown to play a major role in the intrinsic and acquired resistance of a number of human tumors against hydrophobic, natural product drugs. Drugs that act as substrates for and are consequently detoxified by P-gp include the vinca alkaloids (vincristine and vinblastine), anthracyclines (Adriamycin), and epipodophyllotoxins (etoposide). While P-gp associated MDR is a major determinant in tumor cell resistance to chemotherapeutic agents, it is clear that the phenomenon of MDR is multifactorial and involves a number of different mechanisms. One such alternative pathway for resistance to anthracyclines involves the emergence of a 190 kD protein (p190)that is not P-gp. See, T. McGrath, et al., *Biochemical Pharmacolology*, 38:3611 (1989). The protein p190 is not found exclusively on the plasma membrane but rather appears to be localized predominantly in the endoplasmic reticulum. See, e.g., D. Marquardt, and M. S. Center, *Cancer Research*, 52:3157 (1992).

The protein p190 possesses a nucleotide binding domain that is homologous with the ATP binding site of P-gp. See, D. Marquardt, et al., *Cancer Research*, 50:1426 (1990). The mechanism(s) utilized by p190 to confer resistance to ADRIAMYCIN™ is not well understood but may involve the intracellular redistribution of ADRIAMYCIN™ away from the nucleus. See, D. Marquardt and M. S. Center, supra. ADRIAMYCIN™ is an inhibitor of topoisomerase II [W. T. Beck, *Bulletins in Cancer*, 77:1131 (1990)] which is an enzyme involved in DNA replication. Redistribution of ADRIAMYCIN™ away from the nucleus would therefore be an important component in cellular resistance to this drug. The studies published to date on p190 have utilized cell lines selected in vitro for resistance to ADRIAMYCIN™. T. McGrath, et al., supra; D. Marquardt and M. S. Center, supra; and D. Marquardt, et al., *Cancer Research*, supra.

The association of p190 with drug resistance was made by sodium dodecyl sulfate polyacrylamide gel electrophoresis (SDS-PAGE) of radioactive extracts prepared from Adriamycin-resistant HL60/Adr human leukemia cells labeled with 8-azido-alpha[$^{32}$P]ATP. See, T. McGrath, et al., supra. The drug-resistance phenotype conferred by p190 is not limited to the anthracyclines. Epipodophyllotoxin resistance is linked to p190 expression. The $IC_{50}$'s of HL60/S cells treated with ADRIAMYCIN™ and ETOPOSIDE™ were 0.011 µg/ml and 0.39 µg/ml respectively. The $IC_{50}$'s for HL60/Adr cells (a HL60-derived cell line which is resistant to doxorubicin) treated with Adriamycin and Etoposide were 2.2 µg/ml and >10 µg/ml respectively. HL60/S and HL60/Adr cell lines do not express P-glycoprotein. HL60/Adr expresses p190. Thus, resistance to the anthracyclines and epipodophyllotoxins results from p190 expression.

It is, therefore, desirable to provide compounds which are useful for treating resistant neoplasms, the resistant pathway including p190, P-glycoprotein, or both.

SUMMARY OF THE INVENTION

This invention provides a method of reversing multidrug resistance in a multidrug resistant tumor in a mammal which comprising administering to a mammal in need thereof a multidrug resistance reversing amount of a compound of Formula I:

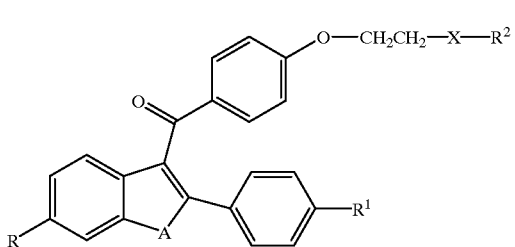

wherein:
A is —O—, —S(O)$_m$—, —N(R$^{11}$)—, —CH$_2$CH$_2$—, or —CH=CH—;
m is 0, 1, or 2;
R$^{11}$ is H, or C$_1$–C$_6$ alkyl;
X is a bond or C$_1$–C$_4$ alkylidenyl;
R$^2$ is a group of the formula

wherein R$^4$ and R$^5$ are independently C$_1$–C$_6$ alkyl or combine to form, along with the nitrogen to which they are attached, a heterocyclic ring selected from the group consisting of hexamethyleneiminyl, piperazino, heptamethyleneiminyl, 4-methylpiperidinyl, imidazolinyl, piperidinyl, pyrrolidinyl, or morpholinyl;
R is hydroxy, halo, hydrogen, C$_3$–C$_8$ cycloalkyl, C$_2$–C$_7$ alkanoyloxy, C$_1$–C$_6$ alkoxy, —OSO$_2$—(C$_1$–C$_{10}$ alkyl),

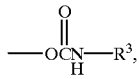

or phenyl, said phenyl being optionally substituted with one, two, or three moieties selected from the group consisting of C$_1$–C$_4$ alkyl, C$_1$–C$_4$ alkoxy, nitro, chloro, or fluoro;
R$^1$ is hydroxy, halo, hydrogen, C$_3$–C$_8$ cycloalkyl, C$_2$–C$_7$ alkanoyloxy, C$_1$–C$_6$ alkoxy, —OSO$_2$—(C$_1$–C$_{10}$ alkyl),

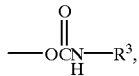

or phenyl, said phenyl being optionally substituted with one, two, or three moieties selected from the group consisting of C$_1$–C$_4$ alkyl, C$_1$–C$_4$ alkoxy, nitro, chloro, or fluoro;
each R$^3$ is independently C$_1$–C$_6$ alkyl, C$_3$–C$_8$ cycloalkyl, unsubstituted or substituted phenyl where the substituent is halo, C$_1$–C$_6$ alkyl or C$_1$–C$_6$ alkoxy;

with the proviso that when X is a bond and A is —S—, R and R$^1$ are not both selected from the group consisting of hydroxy, methoxy, and C$_2$–C$_7$ alkanoyloxy;
or a pharmaceutically acceptable salt or solvate thereof.

The present invention also provides methods for treating a susceptible neoplasm in a mammal which comprises administering a compound of Formula I in combination with an oncolytic agent.

DETAILED DESCRIPTION OF THE INVENTION

The current invention concerns the discovery that a select group of substituted benzofurans, benzothiophenes, indoles, naphthalenes, and dihydronaphthalenes, those of Formula I, are useful as in reversing multidrug resistance in a resistant neoplasm.

The terms and abbreviations used in the instant examples have their normal meanings unless otherwise designated. For example "° C." refers to degrees Celsius; "N" refers to normal or normality; "mmol" refers to millimole or millimoles; "g" refers to gram or grams; "ml" means milliliter or milliliters; "M" refers to molar or molarity; "MS" refers to mass spectrometry; "IR" refers to infrared spectroscopy; and "NMR" refers to nuclear magnetic resonance spectroscopy.

As used herein, the term "C$_1$–C$_{10}$ alkyl" refers to straight or branched, monovalent, saturated aliphatic chains of 1 to 10 carbon atoms and includes, but is not limited to, methyl, ethyl, propyl, isopropyl, butyl, isobutyl, t-butyl, pentyl, isopentyl, and hexyl. The term "C$_1$–C$_{10}$ alkyl" includes within its definition the terms "C$_1$–C$_4$ alkyl" and "C$_1$–C$_6$ alkyl".

"C$_1$–C$_6$ alkoxy" represents a straight or branched alkyl chain having from one to six carbon atoms attached to an oxygen atom. Typical C$_1$–C$_6$ alkoxy groups include methoxy, ethoxy, propoxy, isopropoxy, butoxy, t-butoxy, pentoxy and the like. The term "C$_1$–C$_6$ alkoxy" includes within its definition the term "C$_1$–C$_4$ alkoxy".

"C$_1$–C$_6$ alkylidenyl" refers to a straight or branched, divalent, saturated aliphatic chains of 1 to 6 carbon atoms and includes, but is not limited to, methylenyl, ethylenyl, propylenyl, isopropylenyl, butylenyl, isobutylenyl, t-butylenyl, pentylenyl, isopentylenyl, hexylenyl, and the like. The term "C$_1$–C$_4$ alkylidenyl" is encompassed within the term "C$_1$–C$_6$ alkylidenyl".

The term "halo" encompasses chloro, fluoro, bromo and iodo.

The term "leaving group" as used herein refers to a group of atoms that is displaced from a carbon atom by the attack of a nucleophile in a nucleophilic substitution reaction. The term "leaving group" as used in this document encompasses, but is not limited to, activating groups.

The term "activating group" as used herein refers a leaving group which, when taken with the carbonyl (—C=O) group to which it is attached, is more likely to take part in an acylation reaction than would be the case if the group were not present, as in the free acid. Such activating groups are well-known to those skilled in the art and may be, for example, succinimidoxy, phthalimidoxy, benzotriazolyloxy, benzenesulfonyloxy, methanesulfonyloxy, toluenesulfonyloxy, azido, or —O—CO—(C$_4$–C$_7$ alkyl).

Many of the compounds employed in the present invention are derivatives of naphthalene which are named and numbered according to the RING INDEX, The American Chemical Society, as follows.

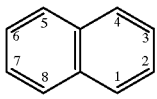

In a similar manner some of the compounds employed in the present invention are derivatives of 1,2-dihydronaphthalene which are named and numbered according to the RING INDEX as follows.

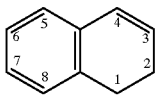

Many of the compounds of the present invention are derivatives of benzofuran which are named and numbered according to the RING INDEX, The American Chemical Society, as follows.

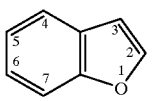

Some of the compounds of the present invention are derivatives of benzo[b]thiophene which are named and numbered according to the RING INDEX as follows.

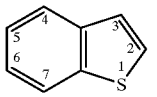

In a similar manner some of the compounds of the present invention are derivatives of indole which are named and numbered according to the RING INDEX as follows.

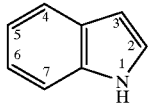

The more preferred compounds employed in the methods of this invention are those compounds of Formula I wherein
a) A is —O—, —S—, —$CH_2$—$CH_2$—, or —CH=CH—;
b) R is hydrogen, hydroxy, $C_1$–$C_3$ alkoxy, or —$OSO_2$—($C_1$–$C_{10}$ alkyl);
c) $R^1$ is hydrogen, hydroxy, $C_1$–$C_3$ alkoxy, or —$OSO_2$—($C_1$–$C_{10}$ alkyl);
d) X is a bond or methylene; and
e) $R^2$ is piperidinyl, hexamethyleneiminyl, pyrrolidinyl, or —$NR^4R^5$, where $R^4$ and $R^5$ are $C_1$–$C_4$ alkyl; and the pharmaceutically acceptable acid addition salts and solvates.

The most preferred compounds employed in the methods of this invention are those compounds of Formula I wherein a) A is —S—;
b) R is hydrogen, hydroxy, $C_1$–$C_3$ alkoxy, or —$OSO_2$—($C_1$–$C_{10}$ alkyl);
c) $R^1$ is hydrogen, hydroxy, $C_1$–$C_3$ alkoxy, or —$OSO_2$—($C_1$–$C_{10}$ alkyl);
d) X is a bond or methylene; and
e) $R^2$ is piperidinyl, hexamethyleneiminyl, pyrrolidinyl, or —$NR^4R^5$, where $R^4$ and $R^5$ are $C_1$–$C_4$ alkyl; and
f) at least one of R and $R^1$ is —$OSO_2$—($C_1$–$C_{10}$ alkyl);

and the pharmaceutically acceptable acid addition salts and solvates thereof.

The compounds of the present invention can be prepared by a variety of procedures well known to those of ordinary skill in the art. The particular order of steps required to produce the compounds of Formula I is dependent upon the particular compound being synthesized, the starting compound, and the relative lability of the substituted moieties.

A. Preparation of Dihydronapthalenyl Compounds

The compounds employed in the present invention in which A is —$CH_2$—$CH_2$— or —CH=CH— may be prepared essentially as described in U.S. Pat. No. 4,230,862, issued to T. Suarez and C. D. Jones on Oct. 28, 1990, which is herein incorporated by reference.

These compounds are generally prepared by the following sequences, the dihydronaphthalene structures in general being precursors to the naphthalene compounds.

The naphthalenes and dihydronaphthalenes employed in the methods of the instant invention may be prepared by reacting a tetralone of Formula II

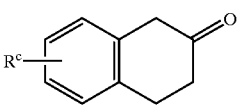

II in which $R^c$ is hydrogen, $C_1$–$C_6$ alkoxy, or benzyloxy with a phenyl benzoate of Formula III

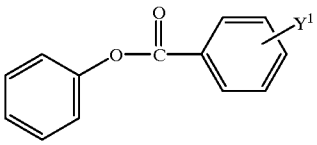

III in which $Y^1$ is methoxy, benzyloxy, or —O—$(CH_2)_n$—$NR^aR^b$, where n is 1–6, and —$NR^aR^b$ is $R^2$. This reaction is generally carried out in the presence of a moderately strong base such as sodium amide and at room temperature or below.

The product which is obtained is a substituted tetralone of Formula IV.

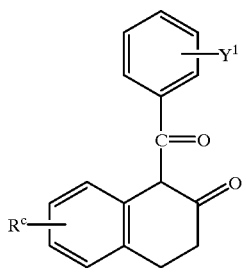

IV

This substituted tetralone is then reacted under Grignard reaction conditions with the Grignard reagent of the formula

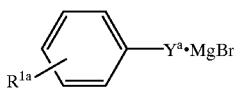

in which $R^{1a}$ is hydrogen, $C_1$–$C_6$ alkoxy, or benzyloxy and $Y^a$ is a bond, methylene, or ethylene.

The compounds which are produced, a 3-phenyl-4-aroyl-1,2-dihydronaphthalenes, have the following formula, Formula V.

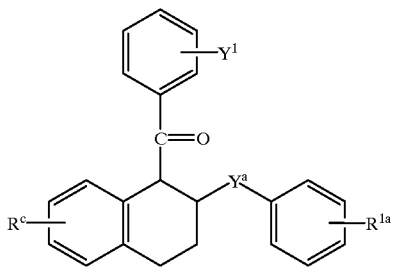

V

In those instances in which $Y^1$ is methoxy, a compound of Formula V can be treated with pyridine hydrochloride at reflux to produce the corresponding hydroxy compound. Under these conditions, should $R^c$ or $R^{1a}$ be alkoxy or benzyloxy, these groups will also be cleaved, resulting in hydroxy groups.

In those instances in which $Y^1$ is methoxy or benzyloxy, and $R^c$ or $R^{1a}$ is alkoxy or benzyloxy, the group at $Y^1$ can be selectively cleaved by treating a compound of Formula V with an equivalent of sodium thioethoxide in N,N-dimethylformamide at a moderately elevated temperature of about 80° C. to about 90° C. The process of the selective cleavage may be monitored by periodic thin layer chromatography analysis. The reaction is complete when little or no starting material remains.

Once the compound of Formula V in which $Y^1$ has been converted to hydroxy has been generated, that compounds can then be treated with a compound of Formula VII

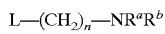    VII

L—(CH$_2$)$_n$—NR$^a$R$^b$   VII wherein L is a good leaving group such as halo, especially chloro. Under the usual reaction conditions, of course, alkylation will be effected at each of the unprotected hydroxy groups which are present in the molecule. This can be avoided, and alkylation at the 4-benzoyl groups alone can be achieved, by carrying out the reaction in the presence of an excess of finely powdered potassium carbonate and using an equivalent or slight excess of the compound of Formula VII.

Depending upon the intended structure of the final product, the compound containing the substituent of Formula VII can then be further treated with an additional quantity of sodium thioethoxide in N,N-dimethylformamide as aforedescribed to effect cleavage of any remaining alkoxy or benzyloxy groups, thereby providing another sequence for achieving formation of those compounds employed in this invention in which $R^1$ and/or $R^2$ are hydroxy.

In any of the above, it is evident that the particular sequence of synthetic steps designed to produce a compound having substituents of particular definition and location is such as one of ordinary skill in the art will well recognize.

In another route for preparing the compounds of Formula I, compounds of Formula VI

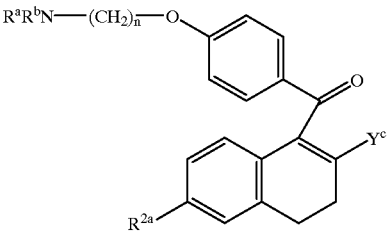

VI wherein: $R^{2a}$ is —H or $C_1$–$C_6$ alkoxy; and $Y^c$ is $C_1$–$C_6$ alkoxy-substituted phenyl or benzyl, are prepared essentially as described by C. D. Jones, et al., *Journal of Medicinal Chemistry*, 53:931–938 (1992), which is herein incorporated by reference.

Generally, a tetralone, as described above, or a salt thereof, is acylated using standard Friedel Crafts conditions to provide a highly enolized diketone of formula VIa

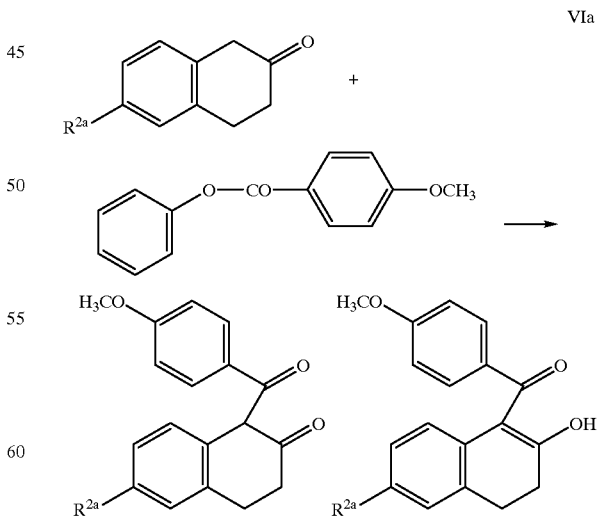

VIa wherein $R^{2a}$ is —H or $C_1$–$C_6$ alkoxy.

Subsequent derivatization using sodium hydride, followed by the addition of diphenyl chlorophosphate, gives the enol phosphate derivative tentatively assigned the Formula VIb

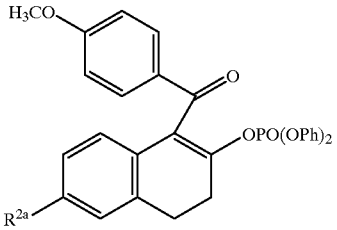

VIb wherein $R^{2a}$ is as defined above.

Addition of phenyl- or benzyl-, substituted phenyl- or substituted benzylmagnesium bromide to a compound of formula VIb, and subsequent selective demethylation provide compounds of formula VIc and VId, respectively, as described by Jones, supra.

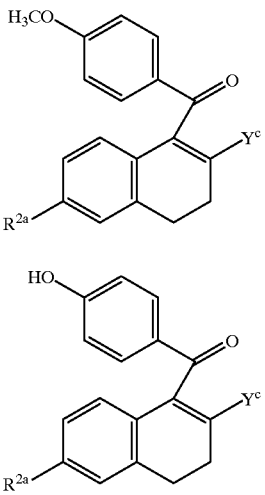

VIc

VId wherein $R^{2a}$ and $Y^c$ are as defined above.

Finally a compound of formula VId is alkylated with a compound of the formula

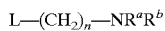

L—(CH$_2$)$_n$—NR$^a$R$^b$ in which L is a bromo or, preferably, a chloro moiety, and $R^{2a}$ and $Y^c$ optionally are dealkylated by standard procedures, to provide compounds of formulae VIe and VIf, respectively.

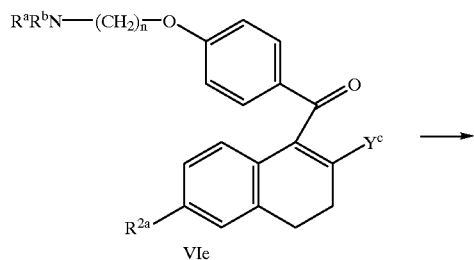

VIe

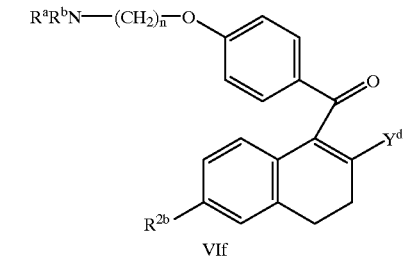

VIf wherein $R^{2b}$ is —H or —OH and $Y^d$ is phenyl, benzyl, hydroxyphenyl, or hydroxybenzyl.

In the process for preparing compounds of formula VIe or VIf, it is evident that the particular sequence of synthetic steps designed to produce a compound having substituents of particular definition and location is such as one of ordinary skill in the art will recognize.

The compounds of Formula VIf can be substituted using standard means, if desired, to produce the corresponding dihydronaphthenyl compounds of Formula I.

B. Preparation of Napthalenyl Compounds

Those compounds of Formula I which are substituted naphthalenes are readily prepared from the corresponding dihydronaphthalenyl compounds. Selective dehydrogenation of the dihydronaphthalene structure to produce specifically the corresponding naphthalene can be accomplished by treatment with 2,3-dichloro-5,6-dicyano-1,4-benzoquinone (DDQ) at a temperature of from about 50° C. to about 100° C. The naphthalene which is produce may be further converted to other naphthalene compounds by means of the derivatizing reactions described supra.

EXAMPLE 1

Preparation of 3-(4-methoxyphenyl)-4-[4-(2-pyrrolidin-1-ylethoxy)benzoyl-1,2-dihydronaphthalene, citrate salt The title compound was prepared as described in U.S. Pat. No. 4,230,862. To a suspension of sodium amide (15.2 g, 0.38 mol) in 250 ml of tertrahydrofuran were added 50 grams (0.34 mol) of β-tetralone. The mixture was stirred for 15–20 minutes, and 78 grams of phenyl p-methoxybenzoate dissolved in tetrahydrofuran were added. The temperature of the reaction mixture was maintained below 10° C., and the mixture was then stirred at room temperature overnight. The reaction mixture was concentrated and the water was added to the residue. The aqueous mixture was extracted with ethyl acetate, and the ethyl acetate extract was washed and concentrated.

The residue was chromatographed on silica using benzene as eluant. The purer fractions obtained by the chromatographic separation were combined and concentrated, and the residue was dissolved in a minimum of methanol. The methanol was cooled, and 35.2 grams of 1-(4-methoxybenzoyl)-2-tetralone were collected by filtration.

4-Bromoanisole (18.7 g, 0.1 mol) was added dropwise in ether to tetrahydrofuran containing 5 drops of 1,2-dibromoethane and 3.6 grams (0.15 mol) of magnesium. Reaction occurred almost immediately, and the addition was continued at a slow rate with evolution of heat sufficient to maintain a general reflux. Upon completion of the addition, the above substituted β-tetralone dissolved in acetone was added dropwise with stirring over a two hour period, the mixture being maintained at 40° C. The resulting mixture was then poured into cold, dilute hydrochloric acid, and the acidic mixture was extracted with ethyl acetate. The ethyl acetate extract was washed, dried, and concentrated to an oil. The oil was chromatographed over silica using benzene as eluant. A subsequent elution of the column with a mixture of benzene containing two percent ethyl acetate yielded 15 grams of 3-(4-methoxyphenyl)-4-(4-methoxybenzoyl)-1,2-dihydronaphthalene as an oil.

A mixture of 11.1 grams (0.03 mol) of the above dimethoxy product, 7.2 grams of sodium hydride (50 percent in oil), and 11 ml of ethyl mercaptan in N,N-dimethylformamide was prepared. The mixture was heated to 65–70° C. and maintained at that temperature for about two hours. The mixture was then cooled and concentrated. The concentrate was acidified and extracted with ethyl acetate. The ethyl acetate extract was washed, dried, and evaporated. The residue was dissolved in benzene and chromatographed over silica to obtain five grams of an oil comprising relatively pure 3-(4-methoxyphenyl)-4-(4-hydroxybenzoyl)-1,2-dihydronaphthalene.

The above phenolic product (4.3 g, 0.01 mol) was dissolved in N,N-dimethylformamide. To this solution was added 0.7 grams of sodium hydride (50 percent in oil), and the resulting mixture was warmed to 40° C. for one hour and then was cooled to room temperature. To the mixture then were added 1.6 grams of 1-chloro-2-pyrrolidinylethane, and the mixture was warmed to 60° C. and maintained at this temperature for about two hours. The reaction mixture was then stirred at room temperature overnight.

The mixture was concentrated, and water was added to the residue. The aqueous mixture was extracted with ethyl acetate. The ethyl acetate extract was washed and concentrated to a residue. The residue was extracted with hexanes, the insoluble portion was dissolved in ethyl acetate, and the ethyl acetate solution was extracted with 1 N hydrochloric acid. The acid extract was rendered alkaline, and then was extracted with ethyl acetate. The ethyl acetate extract was washed and concentrated. One equivalent of citric acid in acetone then was added to the concentrate, and the mixture was concentrated to dryness. The residue was dissolved in a large volume of methyl ethyl ketone. The ketone solution was concentrated to about 300 ml and was cooled to 0° C. The title product, the citrate salt of 3-(4-methoxyphenyl)-4-[4-(2-pyrrolidin-1-ylethoxy)benzoyl-1,2-dihydronaphthalene, was collected by filtration and vacuum dried. mp 82–85° C.

Analysis for $C_{36}H_{39}NO_{10}$: Theory: C, 66.96; H, 6.09; N, 2.17; O, 24.78. Found: C, 66.70; H. 6.27; N, 2.27; O, 24.54.

EXAMPLE 2

Preparation of 3-phenyl-4-[4-(2-pyrrolidin-1-ylethoxy)benzoyl]-7-methoxy-1,2-dihydronaphthalene The title product was prepared as described in U.S. Pat. No. 4,230,862. To 300 ml of N,N-dimethylformamide were added 107 grams of phenyl p-hydroxybenzoate and 26 grams of sodium hydride (50 percent in oil). The mixture was heated to 60° C. and maintained at this temperature for about two hours. To this mixture was added 1-chloro-2-pyrrolidin-1-ylethane (67 g), and the mixture was stirred overnight at 85° C. The bulk of the N,N-dimethylformamide then was evaporated from the mixture. Water was added to the residue, and the aqueous mixture was extracted with ethyl acetate. The ethyl acetate extract was concentrated, and the residue was dissolved in a 1:1 mixture of ether and ethyl acetate. The organic solution was then extracted with 2 N hydrochloric acid, and the acid extract was added dropwise to 2 N sodium hydroxide. The resulting mixture was extracted with ethyl acetate, and the ethyl acetate extract was washed and then dried over magnesium sulfate. The ethyl acetate was concentrated to obtain 110 grams of crude phenyl p-(2-pyrrolidin-1-ylethoxy)benzoate.

To a suspension of 20 grams (0.5 mol) of sodium amide in tetrahydrofuran were added dropwise 41.7 grams of 6-methoxy-2-tetralone in tetrahydrofuran, the temperature of the mixture being maintained below 10° C. Upon completion of the addition, the mixture was stirred for 20 minutes, the reaction mixture being maintained below 10° C., after which time an exothermic reaction occurred, the reaction temperature rising to about 20° C.

The above prepared phenyl p-(2-pyrrolidin-1-ylethoxy)benzoate, dissolved in tetrahydrofuran, was then added dropwise, and the mixture was stirred overnight at room temperature. The mixture was poured into water, and the resulting mixture was extracted with ethyl acetate. The ethyl acetate extract was washed several times with water, and dried over magnesium sulfate. The ethyl acetate was concentrated to obtain about 100 grams of crude material which was dissolved in 1.5 liters of acetone, and one equivalent of citric acid in 400 ml of ethyl acetate was added. The resulting solid was isolated by filtration and vacuum dried to obtain 85.9 grams of 6-methoxy-1-[4-(2-pyrrolidin-1-ylethoxy)benzoyl]-2-tetralone. The product was then chromatographed over silica using ethyl acetate as eluant, and the citrate salt was prepared from the recovered product.

The above product (8.6 g, 0.02 mol) was added to a solution of phenylmagnesium bromide in tetrahydrofuran. The resulting mixture was stirred for one hour at room temperature and then was warmed to 50° C. and maintained at this temperature for three hours. The resulting mixture was poured into a mixture of ice and hydrochloric acid, and the acid mixture was extracted with ethyl acetate. The ethyl acetate extract was washed, dried, and concentrated to obtain 10.5 grams of a red-brown oil. The oil was added to 500 ml of acetic acid, and the mixture was heated on a steam bath for about 30 minutes. The acid was stripped off, and water as added to the residue.

The aqueous mixture was rendered alkaline by addition of base, and the alkaline mixture was extracted with ethyl acetate. The extract was dried and concentrated to obtain 8.7 grams of product which was dissolved in acetone, and one equivalent of citric acid was added to the mixture. The acetone was stripped off, and methyl ethyl ketone was added to the residue. The mixture was maintained at 0° C. overnight, and the crystals which formed were collected by filtration and washed with cold methyl ethyl ketone and vacuum dried. The solid was recrystallized from acetone to obtain the title compound in the form of its citrate salt. mp 98–100° C.

Analysis of $C_{36}H_{39}NO_{10}$: Theory: C, 66.96; H, 6.09; N, 2.17; O, 24.78. Found: C, 66.72; H, 6.27; N, 2.09; O, 24.50.

The title compound in the form of its free base was generated by treatment of the citrate salt with dilute alkali.

Analysis for $C_{30}H_{31}NO_5$: Theory: C, 79.44; H, 6.89; N, 3.09. Found: C, 79.19; H, 6.68; N, 2.91.

EXAMPLE 3

Preparation of 3-phenyl-4-[4-(2-pyrrolidin-1-ylethoxy)benzoyl]-1,2-dihydronaphthalene The title product was prepared as described in U.S. Pat. No. 4,230,862. To a solution of 5.0 grams (18 mmol) of 1-(4-methoxybenzoyl)-2-tetralone (prepared as described in Example 1) in 50 ml of ether was added dropwise at 0° C. a solution of phenylmagnesium bromide (18 mmol) in 9 ml of ether. Upon completion of the addition, the mixture was stirred for twenty minutes. Thin layer chromatography of the reaction mixture indicated the presence of starting material. An additional 13.5 ml of the phenylmagnesium bromide solution were added.

The mixture was refluxed for two hours and then was cooled and poured over iced aqueous ammonium chloride solution. The organic layer was separated and washed with brine. The mixture was then dried over magnesium sulfate, filtered, and evaporated to give about ten grams of a yellow oil. After a wash with hexanes, the product was further purified by chromatography to give 4.67 grams of 3-phenyl-4-(4-methoxybenzoyl)-1,2-dihydronaphthalene.

To 2.0 grams (6 mmol) of the above dihydronaphthalene, dissolved in 10 ml of N,N-dimethylformamide, were added sodium thioethoxide (7.5 mmol), dissolved in 15 ml of N,N-dimethylformamide. The addition was carried out under a nitrogen atmosphere and at 80° C. The mixture was maintained at 80° C. for fifteen hours. The mixture was then cooled and poured into an iced aqueous ammonium chloride solution. The resulting mixture was extracted with ethyl acetate, and the ethyl acetate extract was washed four times with brine.

The ethyl acetate extract was dried over magnesium sulfate an evaporated to give an oil which was further purified by chromatography on a silica column, using benzene to elute impurities. The product was then eluted with ethyl acetate to give, upon evaporation of the ethyl acetate, 1.69 grams of 3-phenyl-4-(4-hydroxybenzoyl)-1,2-dihydronaphthalene as a clear pale yellow oil.

A mixture of 1.61 grams (4.95 mmol) of the above product in 10 ml of dry N,N-dimethylformamide containing 119 mg (4.95 mmol) of sodium hydride and freshly distilled 1-chloro-(2-pyrrolidin-1-yl)ethane. The addition was made under a nitrogen atmosphere with the temperature being maintained at about 10° C. Upon completion of the resulting efferverscence, the mixture was heated to 80° C. and maintained at that temperature for about two hours. The mixture was then poured into water, and the total was extract with ether. The ether extract was washed five times with brine, and dried over magnesium sulfate. The ether layer was then filtered and evaporated to give a gray oil, which was further purified by chromatography to give 3-phenyl-4-[4-(2-pyrrolidin-1-ylethoxy)benzoyl]-1,2-dihydronaphthalene.

The product was converted to the corresponding citrate salt by treatment with 0.59 grams of citric acid in 50 ml of hot acetone. The resulting mixture was evaporated to dryness, and the residue was stirred for about fifteen hours with ether to obtain the citrate salt. mp 89–93° C.

Analysis for $C_{33}H_{37}NO_9 \cdot 0.5 \, H_2O$: Theory: C, 67.34; H, 6.13; N, 2.25. Found: C, 67.06; H, 6.41; N, 2.66.

EXAMPLE 4

Preparation of 1-[4-(2-pyrrolidin-1-ylethoxy)benzoyl]-2-phenylnaphthalene, citrate salt The title product was prepared as described in U.S. Pat. No. 4,230,862. To 30 ml of dioxane were added 3-phenyl-4-(4-methoxybenzoyl)-1,2-dihydronaphthalene (1.90 g, 5.58 mmol), prepared as described in Example 3, supra, and 2,3-dichloro-5,6-dicyano-1,4-benzoquinone (2.00 g, 8.81 mmol). The resulting mixture was heated to reflux and refluxed for twelve hours under a nitrogen atmosphere. The mixture was then cooled and evaporated to dryness. The residue was partitioned between ether and water. The organic fraction was washed 5 N sodium hydroxide (5×20 ml), followed by a wash with brine. The mixture was then dried over magnesium sulfate and evaporated to give 1.9 grams of substantially pure 1-(4-methoxybenzoyl)-2-phenylnaphthalene.

Employing substantially the same demethylation procedure as described in Example 3, 1.83 grams (5.41 mmol) of the above product were treated with sodium thioethoxide to obtain 1.4 grams of 1-(4-hydroxybenzoyl)-2-phenylnaphthalene.

To 10 ml of N,N-dimethylformamide were added 1.25 grams of the above product. The resulting mixture was added at about 10° C. to a mixture of 20 ml of N,N-dimethylformamide containing 120 mg (5.0 mmol) of sodium hydride and 800 mg of 1-chloro-2-(pyrrolidin-1-yl)ethane. Upon completion of the resulting effervescence, the mixture was heated to 80° C. and maintained at that temperature for about three hours, during which time sodium chloride precipitated. The mixture was cooled and evaporated to dryness. The resulting residue was partitioned between water and ethyl acetate. The organic fraction was washed with brine (5×25 ml). The organic fraction was dried and evaporated to give 1.62 grams of 1-[4-[2-(pyrrolidin-1-yl)ethoxy]benzoyl]-2-phenylnaphthalene as a yellow oil.

The above free base was converted to the corresponding citrate salt in accordance with the method of Example 3, employing 0.811 grams of citric acid hydrate. The title compound was obtained as an amorphous solid which crystallized on standing overnight in ether. mp 105–108° C.

Analysis for $C_{33}H_{35}NO_9 \cdot H_2O$: Theory: C, 65.55; H, 5.90; N, 2.22. Found: C, 66.90; H, 5.85; N, 2.25.

EXAMPLE 5

Preparation of 3-(4-methoxyphenyl)-4-[4-[2-(piperidin-1-yl)ethoxy]benzoyl]-1,2-dihydronaphthalene, citrate salt The title compound was prepared as described in U.S. Pat. No. 4,230,862. To a suspension of sodium hydride (0.269 g, 11 mmol), washed free of mineral oil, and 1-chloro-2-

(piperidin-1-yl)ethane (1.82 g, 12 mmol) in N,N-dimethylformamide (50 ml) at 0° C., and under a nitrogen atmosphere, were added 4.0 grams (10 mmol) of 3-(4-methoxyphenyl)-4-(4-hydroxybenzoyl)-1,2-dihydronaphthalene, prepared as described in Example 1, dissolved in 20 ml of N,N-dimethylformamide. The solution was added dropwise with stirring. When the effervescence had ceased for the most part, the mixture was heated to 50° C. and maintained at that temperature for several hours. The progress of the reaction was monitored by thin layer chromatography.

Once the reaction had progressed sufficiently, the N,N-dimethylformamide was evaporated, and the concentrated mixture was poured over ice water and ethyl acetate. The ethyl acetate fraction was washed with brine, dried over potassium carbonate, filtered, and evaporated, The resulting oil was chromatographed over a 1.5"×12" silica column using the following as a double gradient:

(i) 10 percent ethyl acetate in benzene (500 ml)→20 percent ethyl acetate in benzene (2 liters);

(ii) 20 percent ethyl acetate in benzene (1.5 liters)→1:1 mixture of methanol and ethyl acetate (1.5 liters).

The appropriate fractions were concentrated to give an almost colorless oil. The oil was dissolved in ethyl acetate, and the ethyl acetate solution was dried over potassium carbonate, filtered, and evaporated to give 4.7 grams of the free base of the title compound as a pale yellow oil.

The free base (3.4 g, 7.28 mmol) was treated with citric acid monohydrate (1.49 g, 7.1 mmol) in about 20 ml of boiling acetone. When a clear solution was obtained, the acetone was evaporated, 300 ml of anhydrous ether was added, and the resulting precipitate was stirred overnight. The title compound (5.2 grams) was collected as a white powder.

Analysis for $C_{37}H_{41}NO_{10}$: Theory: C, 67.36; H, 6.26; N, 2.12. Found: C, 67.25; H, 5.96; N, 1.84.

EXAMPLE 6

Preparation of 3-(4-methoxyphenyl)-4-[4-(2-dimethylaminoethoxy)benzoyl]-1,2-dihydronaphthalene, citrate salt The title compound was prepared as described in U.S. Pat. No. 4,230,862. To 50 ml of acetone were added 4.0 grams (11.2 mmol) of 3-(4-methoxyphenyl)-4-(4-hydroxybenzoyl)-1,2-dihydronaphthalene, prepared as described in Example 1, 1.81 grams (16.8 mmol) of 1-chloro-2-dimethylaminoethane (freshly prepared from the hydrochloride), and 2.32 grams (16.8 mol) of finely powdered potassium chloride. The resulting mixture was refluxed under nitrogen with stirring for about 72 hours. The progress of the reaction was monitored by thin layer chromatography.

The resulting mixture was then poured over ice, and the resulting mixture was extracted with ether. The ether was washed three times with brine, dried over potassium carbonate, filtered, and evaporated to obtain 4.51 grams of the free base of the title compound as a brown oil.

The oil was vacuum dried and then was converted to the citrate salt by treatment with 2.17 grams (10.4 mmol) of citric acid monohydrate in 50 ml of hot acetone. Evaporation of the acetone and stirring of the residue with ether gave 5.2 grams of the title compound as an amorphous solid.

Analysis for $C_{34}H37NO_{10}$: Theory: C, 65.90; H, 6.02; N, 2.26. Found: C, 66.17; H, 6.23; N, 2.37.

EXAMPLE 7

Preparation of 3-(4-hydroxyphenyl)-4-[4-[2-(pyrrolidin-1-yl)ethoxy]benzoyl]-1,2-dihydronaphthalene, mesylate salt The title compound was prepared as described in U.S. Pat. No. 4,230,862. To 25 ml of methyl ethyl ketone were 10 grams (2.92 mmol) of 3-(4-hydroxyphenyl)-4-(4-hydroxybenzoyl)-1,2-dihydronaphthalene, 0.497 grams (2.92 mmol) of 1-chloro-2-(pyrrolidin-1-yl)ethane, and 1.21 grams (8.77 mmol) of finely powdered potassium carbonate. The resulting mixture was refluxed for 16 hours. The mixture was then cooled and poured into a mixture of water and ethyl acetate. The resulting mixture was rendered acidic by addition of 1 N hydrochloric acid and then alkaline by the addition of sodium bicarbonate.

The organic fraction was washed with brine, dried over magnesium sulfate, and evaporated to give a yellow oil. The resulting oil was further purified by chromatography. The free base (362 mg, 0.825 mmol) as converted to the mesylate salt by treatment with an equivalent of methanesulfonic acid in acetone to yield the title compound as an amorphous solid.

Analysis for $C_{31}H_{37}NO_6S$: Theory: C, 67.27; H, 6.21; N, 2.61. Found: C, 67.25; H, 6.19; N, 2.69.

EXAMPLE 8

Preparation of 3-(4-methoxyphenyl)-4-[4-[2-(hexamethyleneimin-1-yl)benzoyl]-1,2-dihydronaphthalene, mesylate salt The title compound was prepared as described in U.S. Pat. No. 4,230,826. To 50 ml of methyl ethyl ketone were added 3.0 g (8.43 mmol) of 3-(4-methoxyphenyl)- 4-(4-hydroxybenzoyl)-1,2-dihydronaphthalene, 1.84 g (9.27 mmol) of 1-chloro-2-(hexamethyleneimin-1-yl)ethane hydrochloride, and 3.25 grams (25.3 mmol) of finely powdered potassium carbonate. The mixture was refluxed for 48 hours.

The mixture was then poured into water, and ethyl acetate was added. The resulting organic layer was separated, washed with brine, dried, and evaporated to a yellow oil. The oil was further purified by chromatography. The free base of the title compound was recovered (2.51 g) as a pale yellow oil. The oil was treated with 0.431 g (4.48 mmol) of methanesulfonic acid in 10 ml of acetone. Upon scratching and cooling of the mixture, crystals formed. The mixture was cooled overnight and 1.97 grams of the title compound were obtained as a white crystals. mp 123–125° C.

Analysis for $C_{34}H_{41}NO6S$: Theory: C, 68.61; H, 6.80; N, 2.42. Found: C, 68.38; H, 6.62; N, 2.40.

EXAMPLE 9

Preparation of 3-(4-methoxyphenyl)-4-[4-[2-(piperidin-1-yl)ethoxy]benzoyl]-1,2-dihydronaphthalene, mesylate salt The title compound was prepared as described in U.S. Pat. No. 4,230,862. To 150 ml of methyl ethyl ketone were added 7.8 g (21.9 mmol) of 3-(4-methoxyphenyl)-4-(4-hydroxybenzoyl)-1,2-dihydronaphthalene, 4.84 grams (23.6 mmol) of 1-chloro-2-(piperidin-1-yl)ethane hydrochloride, and 14.5 grams (109 mmol) of potassium carbonate. The resulting mixture was refluxed overnight.

The mixture was then poured into a mixture of water and ethyl acetate. The resulting organic fraction was separated, washed with brine, dried over magnesium sulfate, and evaporated in vacuo to obtain the free base of the title compound as a yellow oil.

The oil was dissolved in 30 ml of acetone and was treated with 2.105 grams (21.9 mmol) of methanesulfonic acid. The mixture was cooled and scratched, and the title compound was collected at −40° C. and ashed well with acetone and ether cooled to about −60° C. The solid was then vacuum dried at 100° C. to obtain 11.21 grams of the title compound as a white crystalline solid. mp 157–158° C.

Analysis for $C_{33}H_{39}NO_6S$: Theory: C, 68.18; H, 6.62; N, 2.48. Found: C, 68.11; H, 6.76; N, 2.50.

EXAMPLE 10

Preparation of 3-(4-methoxyphenyl)-4-(4-diethylaminoethoxybenzoyl)-1,2-dihydronaphthalene, mesylate salt To 75 ml of methyl ethyl ketone were added 4.0 grams (11.2 mmol) of 3-(4-methoxyphenyl)-4-(4-hydroxybenzoyl)-1,2-dihydronaphthalene, 2.41 grams (14 mmol) of 1-chloro-2-diethylaminoethane hydrochloride, and 7.93 grams (56 mmol) of finely powdered potassium carbonate. The mixture was refluxed overnight, and, employing the method of Example 9, 5.67 grams of the free base of the title compound were obtained as a yellow oily material.

The oil was treated with 1.07 grams (11.2 mmol) of methanesulfonic acid in about 15 ml of acetone. The resulting mixture was maintained with cooling for several days after which white crystals appeared. The crystals were somewhat hygroscopic and were collected as quickly as possible and vacuum-dried. There were obtained 4.3 grams of the title compound as a white crystalline solid.

Analysis for $C_{31}H_{39}NO_6S$: Theory: C, 67.24; H, 7.10; N, 2.53. Found: C, 67.48; H, 6.92; N, 2.43.

EXAMPLE 11

Preparation of 3-(4-methoxyphenyl)-4-(4-diisopropylaminoethoxybenzoyl)-1,2-dihydronaphthalene, mesylate salt To 75 ml of methyl ethyl ketone were added 3.84 grams (10.8 mmol) of 3-(4-methoxyphenyl)-4-(4-hydroxybenzoyl)-1,2-dihydronaphthalene, 2.70 grams (13.5 mmol) of 1-chloro-2-diisopropylaminoethane hydrochloride, and 7.11 grams (54 mmol) of finely powdered potassium carbonate. The mixture was allowed to reflux overnight, and, upon workup, in accordance with the procedure of Example 9, 5.64 grams of the free base of the title compound were obtained as a yellow oily substance. The oily product was treated with 1.04 grams (10.8 mmol) of methanesulfonic acid in about 25 ml of acetone. The mixture was cooled, and crystals slowly appeared. The crystals collected at −40° C. with the aid of acetone cooled to −60° C. Vacuum drying of the product gave 5.1 grams.

Analysis for $C_{33}H_{41}NO_6S$: Theory: C, 68.37; H, 7.31; N, 2.42. Found: C, 68.08; H, 6.91; N, 2.21.

The following compounds were prepared essentially as described in the above examples:

EXAMPLE 12

3-hydroxy-4-[4-[2-(pyrrolidin-1-yl)ethoxy]benzoyl]-1,2-dihydronaphthalene, sodium salt

EXAMPLE 13

2-(4-methoxyphenyl)-1-[4-[2-(pyrrolidin-1-yl)ethoxy]benzoyl]naphthalene, mesylate salt

EXAMPLE 14

3-(4-methoxyphenyl)-4-[4-[2-(piperidin-1-yl)ethoxy]benzoyl]-7-methoxy-1,2-dihydronaphthalene, mesylate salt

EXAMPLE 15

3-(4-methoxyphenyl)-4-[4-(2-dimethylaminoethoxy)benzoyl]-1,2-dihydronaphthalene, 2-hydroxy-1,2,3-propanetricarboxylic acid salt

EXAMPLE 16

3-(4-methoxyphenyl)-4-[4-[2-(N-methyl-1-pyrrolidinium)ethoxy]benzoyl]-1,2-dihydronaphthalene, iodide salt

EXAMPLE 17

3-(4-methoxyphenyl)-4-[4-[2-(pyrrolidin-1-yl)ethoxy]benzoyl]-1,2-dihydronaphthalene, mesylate salt C. Preparation of Indoles, Benzofurans and Benzothiophenes The benzofurans, benzothiophenes and indoles employed in the methods of the instant invention were made essentially as described in U.S. Pat. No. 4,133,814, issued Jan. 9, 1979, U.S. Pat. No. 4,418,068, issued Nov. 29, 1983, and U.S. Pat. No. 4,380,635, issued Apr. 19, 1983, all of which are herein incorporated by reference. This process provides a convenient process which acylates a methylated starting compound and then optionally demethylates it to obtain the desired dihydroxy product. The acylation and demethylation may be performed in successive steps in a single reaction mixture or the intermediate may be isolated and the demethylation step be performed in a separate reaction.

The methyl-protected compound of Formula VII

VII

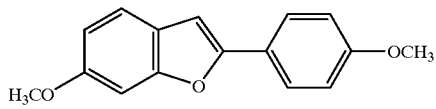

is most easily obtained by reacting 3-methoxyphenol and α-bromo-4-methoxyacetophenone in the presence of a strong base at a relatively low temperature, to form α-(3-methoxyphenoxy)-4-methoxyacetophenone, which is then ring closed with an agent such as polyphosphoric acid at a high temperature to obtain the intermediate compound of Formula VII.

The acylation of this invention is a Friedel-Crafts acylation, and is carried out in the usual way, using aluminum chloride or bromide, preferably the chloride, as the acylation catalyst.

The acylation is ordinarily carried out in a solvent, and any inert organic solvent which is not significantly attacked by the conditions may be used. For example, halogenated solvents such as dichloromethane, 1,2-dichloroethane, chloroform, and the like may be used, as can aromatics such as benzene, chlorobenzene, and the like. It is preferred to use a halogenated solvent, especially dichloromethane.

It has been found that toluene is rather easily acylated under the conditions used in the Friedel-Crafts acylation, and so it is important, when toluene is used in an earlier step of the process, to remove it as completely as possible from the protected starting compound, to avoid wasting the acylating agent.

The acylations may be carried out at temperatures from about −30° C. to about 100° C., preferably at about ambient temperature, in the range of from about 15° C. to about 30° C.

The acylating agent is an active form of the appropriate benzoic acid of Formula VIII

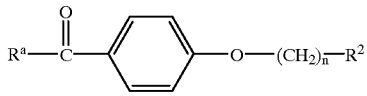

VIII wherein $R^a$ is chloro or bromo. The preferred acylating agents are those wherein $R^a$ is chloro. Thus, the most highly preferred individual acylating agents are 4-[2-(piperidin-1-yl)ethoxy]benzoyl chloride, 4-[2-(hexamethyleneimin-1-yl) ethoxy]benzoyl chloride, 4-[2-(pyrrolidin-1-yl)ethoxy] benzoyl chloride, 4-[2-(dimethylamino)ethoxy]-benzoyl chloride, 4-[2-(diethylamino)ethoxy]benzoyl chloride, and 4-[2-(diisopropylamino)ethoxy]benzoyl chloride.

The acyl chloride used as an acylating agent may be prepared from the corresponding carboxylic acid by reaction with a typical chlorinating agent such as thionyl chloride. Care must be taken to remove any excess chlorinating agent from the acyl chloride. Most conveniently, the acyl chloride is formed in situ, and the excess chlorinating agent is distilled off under vacuum.

It is generally preferred that an equimolar amount of the compounds of Formula VII and VIII are reacted together. If desired, a small excess of either reactant may be added to assure the other is fully consumed. It is generally preferred to use a large excess of the acylation catalyst, such as about 2–12 moles per mole of product, preferably about 5–10 moles of catalyst per mole of product.

The acylation is rapid. Economically brief reaction times, such as from about 15 minutes to a few hours provide high yields of the acylated intermediate. Longer reaction times may be used if desired, but are not usually advantageous. As usual, the use of lower reaction temperatures call for relatively longer reaction times.

The acylation step is ended and the optional demethylation step is begun by the addition of a sulfur compound selected from the group consisting of methionine and compounds of the formula $$X^1\text{—S—}Y^\alpha$$

wherein $X^1$ is hydrogen or unbranched $C_1$–$C_4$ alkyl, and $Y^\alpha$ is $C_1$–$C_4$ alkyl or phenyl. The sulfur compounds are, preferably, the alkylthiols, such as methanethiol, ethanethiol, isopropanethiol, butanethiol, and the like; dialkyl sulfides, such as diethyl sulfide, ethyl propyl sulfide, butyl isopropyl sulfide, dimethyl sulfide, methyl ethyl sulfide, and the like; benzenethiol; methionine; and alkyl phenyl sulfides, such as methyl phenyl sulfide, ethyl phenyl sulfide, butyl phenyl sulfide, and the like.

It has been found that demethylation is most efficient when a substantial excess of the sulfur compound is used, in the range of about 4 to about 10 moles per mole of the starting benzofuran. The process may be carried out, although less efficiently, with a smaller amount of the sulfur compound (in the range of about 2 to 3 moles per mole of the starting compound). It is also possible to use a small amount of the sulfur compound, and to improve the yield by the addition of about 1 to 3 moles of an alkali metal halide, such as sodium, potassium, or lithium chloride, bromide, or iodide.

The demethylation reaction goes well at about ambient temperature, in the range of from about 15° C. to about 30° C., and such operation is preferred. The demethylation may be carried out, however, at temperatures in the range of from about −30° C. to about 50° C. if it is desired to do so. Short reaction times, in the range of about one hour, have been found to be sufficient.

After the product has been demethylated, it is recovered and isolated by conventional means. It is customary to add water to decompose the complex of the acylation catalyst. Addition of dilute aqueous acid is advantageous. The product precipitates in many instances, or may be extracted with an organic solvent according to conventional methods. The examples below further illustrate the isolation.

In an alternative process an intermediate compound of Formula IX

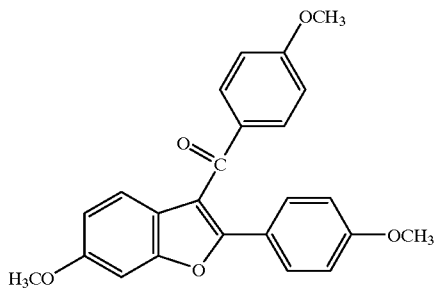

IX is synthesized by the reaction of 2-hydroxy-4-methoxybenzaldehyde and 1-(4-methoxyphenyl)-2-(4-methoxyphenyl)ethanone, essentially as described in Preparation 3a, infra. This reaction usually employs equimolar amounts of the two reactants although other ratios are operable. The reaction is performed in a non-reactive solvent such as ethyl acetate, chloroform, and the like, in the presence of an acid. Hydrochloric acid, particularly when created by bubbling anhydrous hydrogen chloride, is an especially preferred acid. Lower alkyl alcohols are usually added to the non-polar solvent so as to retain more of the hydrochloric acid created in situ, with ethanol and methanol being especially preferred. The reaction is performed at temperatures ranging from ambient temperature up to the reflux temperature of the mixture. This reaction results in the synthesis of a compound of Formula X

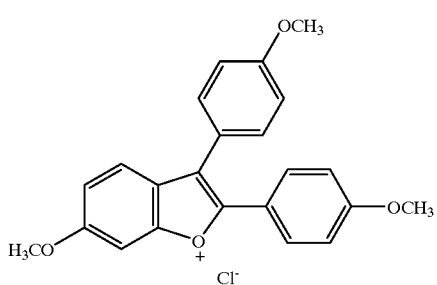

X or an equivalent anion if hydrochloric acid is not used, which is then oxidized to the compound of Formula IX by the addition of hydrogen peroxide. The intermediate of Formula X may be isolated or may preferably be converted to the compound of Formula IX in the same reaction vessel.

The compound of Formula IX is then selectively demethylated, essentially as described in Preparation 4a, infra to yield the compound of Formula XI

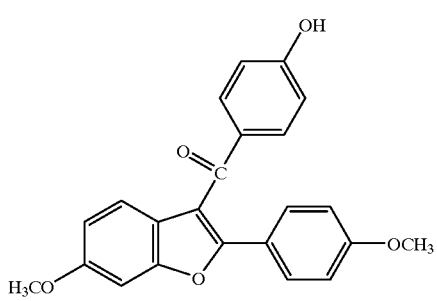

XI

The ether of the compounds of Formula I is then produced by the substitution of the hydrogen on the hydroxy group by an alkyl or halide.

Those compounds of Formula I in which "A" equals —N($R^{11}$)— are prepared in essentially the same manner as the substituted benzofurans described supra. Example 33, infra, provides one such protocol for synthesizing the substituted indoles of this invention.

Those compounds of Formula I in which "A" equals —S(O)$_m$— are prepared in essentially the same manner as the substituted benzofurans described supra. The examples infra provide several exemplifications of these benzothiophenes and the oxidated derivatives thereof.

Those compounds of Formula I in which m is one or two may be prepared by oxidation of the corresponding benzothiophene in which m is zero. Oxidation may be carried out by treating the benzothiophene with an oxidizing agent, for example, m-chloroperbenzoic acid, or the like, for a time sufficient to achieve formation of the sulfoxide group. The progress of the oxidation reaction may be monitored by thin layer chromatography methods.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dicarboxylate, hexyne-1,4-dicarboxylate, caprate, caprylate, cinnamate, citrate, formate, fumarate, glycollate, heptanoate, hippurate, hydrochloride, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferable salt is the hydrochloride salt.

The pharmaceutically acceptable acid addition salts are typically formed by reacting a compound of Formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides and carbonates, as well as aliphatic and aromatic amines, aliphatic diamines and hydroxy alkylamines. Bases especially useful in the preparation of addition salts include ammonium hydroxide, potassium carbonate, calcium hydroxide, methylamine, diethylamine, ethylene diamine, cyclohexylamine and ethanolamine.

The pharmaceutically acceptable salts frequently have enhanced solubility characteristics compared to the compound from which they are derived, and thus are often more amenable to formulation as liquids or emulsions.

EXAMPLES

The following experiments illustrate the preparation of the benzofurans, benzothiophenes and indoles employed in the present invention. The terms "NMR", "IR" or "MS" following a synthesis protocol indicates that the nuclear magnetic resonance spectrum, infrared spectrum, or the mass spectrometry was performed and was consistent with the title product.

Preparation 1a

Synthesis of 2-(3-methoxyphenoxy)-1-(4-methoxyphenyl)ethanone

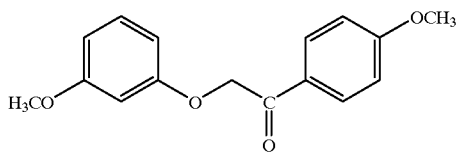

In a one liter round-bottom flask, fitted with a condenser and nitrogen inlet, were added 3-methoxyphenol (12.4 g, 0.1 mole), 4-methoxyphenacyl bromide (22.9 g, 0.1 mole), potassium carbonate (17.3 g, 0.125 mole) in 100 ml of 2-butanone. This mixture was heated to 80° C. and was maintained at this temperature for about four hours. The progress of the reaction was monitored by thin layer chromatography (silica gel, 9:1 toluene:ethyl acetate).

After the four hours at 80° C. the reaction mixture was cooled and the reaction mixture was partitioned by the addition of water. The organic phase was removed and the aqueous layer was washed with 2-butanone. The organic layers were then combined, dried over magnesium sulfate, and the solvents were removed in vacuo to yield 31.1 grams of a yellow oil. The yellow oil was further purified by chromatography, the fractions containing the desired product were then crystallized. All of the crystalline fractions were combined and then dissolved in 80 ml of hot ethanol. Fifteen milliliters of hot water was then added, the product was crystallized, and subsequently washed with an ethanol/water mixture to yield 19.1 g (70%) of the desired title product. mp 52.5°–53.5° C.

Analysis for $C_{16}H_{16}O_4$: Theory: C, 68.08; H, 5.71; N, 2.84. Found: C, 67.86; H, 5.51; N, 2.88.

Preparation 2a

Synthesis of 2-methoxyphenyl-6-methoxybenzofuran

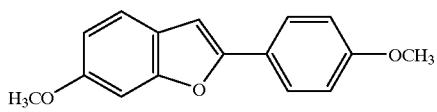

The cyclization of the product of Preparation 1a was performed essentially as described in C. Goldenberg, et al., *Chimie Therapeutique*, 398–411 (1973). In a 500 ml 3-neck round bottom flask polyphosphoric acid (30 g) was added to 200 ml of xylene. The mixture was then heated to about 120° C. To this heated mixture was then added 2-(3-methoxyphenoxy)-1-(4-methoxyphenyl)ethanone (10 g, 0.037 mole), prepared as described supra, and the temperature was raised to about 170° C., and maintained at that temperature for about eight hours. The reaction mixture was then cooled and water was added.

The dark aqueous layer was separated from the yellow organic phase. The organics were washed with water and by aqueous sodium carbonate, and then dried over anhydrous magnesium sulfate. The solvents were removed in vacuo, resulting in a yellow-orange solid. The product was recrystallized from a minimum of hot acetone, followed by the addition of ethanol and water. The residual acetone was removed by boiling. Cooling to room temperature yielded white crystals (2.09 g, 22% yield). mp 158° C.

Analysis for $C_{16}H_{14}O_3$: Theory: C, 75.58; H, 5.55; O, 18.88. Found: C, 75.33; H, 5.67; O, 18.62.

Preparation 3a

Synthesis of 2-(4-methoxyphenyl)-3-(4-methoxybenzoyl)-6-methoxybenzofuran

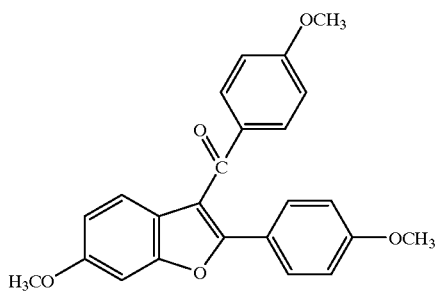

In a 250 ml 3-neck round bottom flask were added 2-hydroxy-4-methoxybenzaldehyde (10 g, 65.7 mmol), 1-(4-methoxyphenyl)-2-(4-methoxyphenyl)ethanone (16 g, 62.6 mmol), ethyl acetate (100 ml) and ethanol (25 ml). The reaction mixture was then warmed to about 45° C. until all the starting materials were dissolved. Hydrogen chloride gas was then bubbled in for about 30 minutes, resulting in the formation of a bright red coloration. The reaction was then allowed to stand at room temperature for about two hours at which time the solvents were removed in vacuo to leave a bright red oil.

The red oil was dissolved in 180 ml of methanol and 30 ml of 20% sulfuric acid was added with stirring and cooling. Hydrogen peroxide (30 ml) was added dropwise and the mixture was allowed to stir for about 30 minutes. A saturated sodium chloride solution (500 ml) and ethyl acetate (300 ml) were added to the reaction mixture and the organic fraction was removed. The organic layer was washed with a saturated sodium chloride solution, dried, and the solvents were removed in vacuo to provide 25 g of a reddish brown oil which was further purified by chromatography to yield the title product (1.25 g) as a yellow oil. mp 106–109° C.

Analysis for $C_{24}H_{20}O_5$: Theory: C, 74.21; H, 5.19; O, 20.60. Found: C, 74.07; H, 5.22; O, 20.38.

Preparation 4a

Synthesis of 2-(4-methoxyphenyl)-3-(4-hydroxybenzoyl)-6-methoxybenzofuran

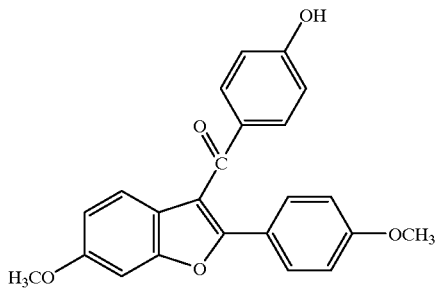

In a three-neck round bottom flask under a nitrogen atmosphere and cooled in an ice bath, ethanethiol (0.95 ml, 1.288 mmol) was dissolved in 10 ml of anhydrous N,N-dimethylformamide. To this solution was added n-butyllithium (0.60 ml of a 1.6 M in hexane solution, 0.966 mmole) followed by the addition of 2-(4-methoxyphenyl)-3-(4-methoxybenzoyl)-6-methoxybenzofuran (250 mg, 0.644 mmole), prepared as described in Preparation 3, supra. The reaction mixture was then heated to 80° C. and allowed to remain at that temperature for about 16 hours.

The reaction mixture was then poured into 1 N hydrochloric acid and extracted with ethyl acetate. The organic layer was then washed with a saturated sodium chloride solution, dried over magnesium sulfate, filtered and the solvents were removed in vacuo. The desired product was further purified by column chromatography. The product was then crystallized from methanol yielding 130 mg (81%) of the desired product. mp 148–149° C.

Analysis for $C_{23}H_{18}O_5$: Theory: C, 73.79; H, 4.85; O, 21.37. Found: C, 73.68; H, 5.12; O, 21.17.

EXAMPLE 18

Synthesis of 2-(4-methoxyphenyl)-3-[4-[2-(piperidin-1-yl)ethoxy]benzoyl]-6-methoxybenzofuran

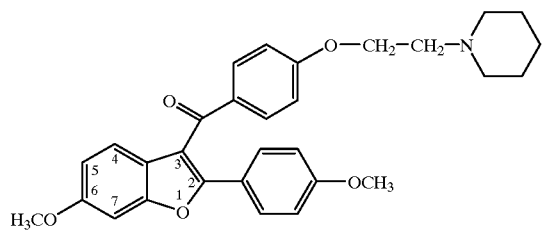

Method A: Acylation of Benzofuran

4-[2-(Piperidin-1-yl)ethoxy]benzoyl chloride (0.562 g, 1.96 mmol) was added to ethylene chloride (20 ml), followed by the addition of 2-methoxyphenyl-6-methoxybenzofuran (0.500 g, 1.96 mmol), prepared as described in Preparation 2a, supra. This mixture was stirred at room temperature as aluminum trichloride (1.96 g, 14.7 mmol) was added. This reaction mixture was then stirred overnight.

The reaction mixture was then poured over ice, and extracted with warm chloroform (3×50 ml). The chloroform was removed by evaporation. Sodium carbonate, water and ethyl acetate were then added and the organic layer was removed, dried over magnesium sulfate, and the solvents were removed in vacuo to provide a yellow oil. The desired product was further purified by chromatography of the yellow oil to yield the desired title product.

NMR, IR, MS. Analysis for $C_{30}H_{31}NO_5$: Theory: C, 74.21; H, 6.44; N, 2.88; O, 16.47. Found: C, 74.11; H, 6.71; N, 2.75; O, 16.57.

Method B: Alkylation of 2-(4-methoxyphenyl)-3-(4-hydroxybenzoyl)-6-methoxybenzofuran In 100 ml of anhydrous N,N-dimethylformamide in a 500 ml round bottom flask were added 2-(4-methoxyphenyl)-3-(4-hydroxybenzoyl)-6-methoxybenzofuran (10.50 g, 28 mmol), prepared as described in Preparation 4a, supra, and potassium carbonate (6.20 g, 34 mmol). This mixture was heated to 100° C. and then 2-(piperidin-1-yl)ethyl chloride (6.20 g, 34 mmol) was added gradually. The reaction mixture was kept at 100° C. for about one hour.

The N,N-dimethylformamide was evaporated and the residue was dissolved in ethyl acetate and water. The ethyl acetate layer was removed and the aqueous layer was washed with more ethyl acetate. The organic fractions were combined, dried over magnesium sulfate, and the solvents were removed in vacuo, yielding 13.3 g of a yellow oil which crystallized upon standing. The product was recrystallized from methanol cooled to −30° C. prior to filtration, yielding 11.4 g (84%) of the desired product as pale yellow crystals. mp 87–89° C.

Analysis for $C_{30}H_{31}NO_5$: Theory: C, 74.21; H, 6.44; N, 2.88; O, 16.47. Found: C, 74.31; H, 6.34; N, 2.63; O, 16.47.

EXAMPLE 19

Synthesis of 2-(4-hydroxyphenyl)-3-[4-[2-(piperidin-1-yl)ethoxy]benzoyl]-6-hydroxybenzofuran

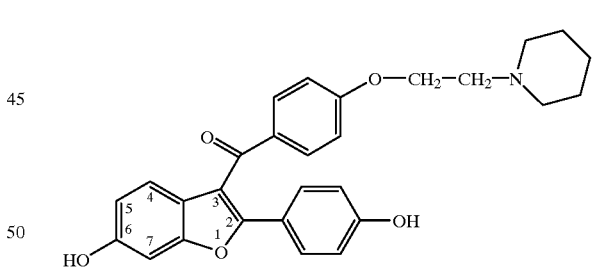

The title product was prepared by the demethylation of 2-(4-methoxyphenyl)-3-[4-[2-(piperidin-1-yl)ethoxy]benzoyl]-6-methoxybenzofuran, the product of Preparation 1a, supra. In a 250 ml three-neck round bottom flask were combined ethylene chloride (50 ml) and aluminum trichloride (9.60 g, 72 mmol) and ethanethiol (6.39 g, 103 mmol) to create a pale yellow liquid. To this liquid was then added the product of Example 1a(5.00 g, 10.3 mmol) in a gradual fashion. A red oil precipitated and the mixture was stirred for about 20 minutes. After cooling the reaction mixture in an ice bath 100 ml of tetrahydrofuran was added and the mixture was allowed to stir until all of the oil had gone into solution.

The reaction mixture was then poured over ice (200 ml) and water (500 ml) and concentrated hydrochloric acid (10 ml) were added. The oil which precipitated was separated from the liquid by decantation. The liquid was extracted with chloroform (warm, 2×300 ml). The oil was dissolved by mixing with ethyl acetate, chloroform, sodium bicarbonate, and a small amount of sodium hydroxide. The chloroform extract and the dissolved oil were transferred to separatory funnel and washed with sodium bicarbonate. The organic phase was then dried over magnesium sulfate and the solvents were removed by evaporation to yield a yellow foam, which was further purified by high performance liquid chromatography.

NMR, IR, MS. Analysis for $C_{28}H_{27}NO_5$: Theory: C, 73.51; H, 5.95; N, 3.06. Found: C, 70.45; H, 6.34; N, 4.02.

EXAMPLE 20

Synthesis of 2-(4-methoxyphenyl)-3-[4-[2-(pyrrolidin-1-yl)ethoxy]benzoyl]-6-methoxybenzofuran hydrochloride

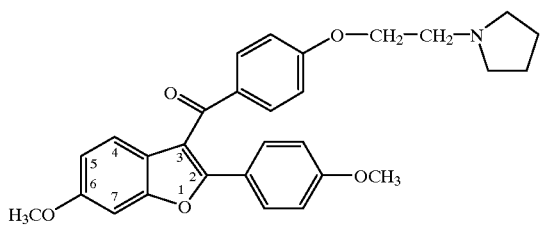

The title compound is prepared essentially as described in the process for preparing the compound of Example 18 except that 4-[2-(pyrrolidin-1-yl)ethoxy]benzoyl chloride is employed in the synthesis of Method A in place of 4-[2-(piperidin-1-yl)ethoxy]benzoyl chloride or 2-(pyrrolidin-1-yl)ethyl chloride is employed in the synthesis of Method B in place of the 2-(piperidin-1-yl)ethyl chloride.

EXAMPLE 21

Synthesis of 2-(4-hydroxyphenyl)-3-[4-[2-(pyrrolidin-1-yl)ethoxy]benzoyl]-6-hydroxybenzofuran hydrochloride

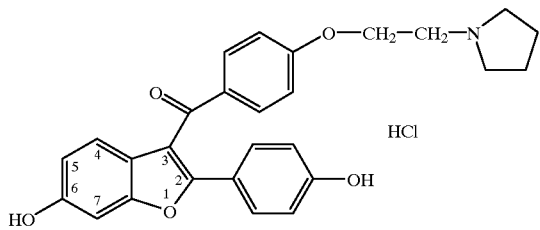

The title compound is prepared essentially as described in Example 19 except that 2-(4-methoxyphenyl)-3-[4-[2-(pyrrolidin-1-yl)ethoxy]benzoyl]-6-methoxybenzofuran is used as the starting material instead of 2-(4-methoxyphenyl)-3-[4-[2-(piperidin-1-yl)ethoxy]benzoyl]-6-methoxybenzofuran.

NMR, IR, MS. Analysis for $C_{27}H_{26}NO_5Cl$: Theory: C, 67.57; H, 5.46; N, 2.92. Found: C, 67.84; H, 5.56; N, 2.87.

EXAMPLE 22

Synthesis of 2-(4-methoxyphenyl)-3-[4-[2-(diethylamino)ethoxy]benzoyl]-6-methoxybenzofuran

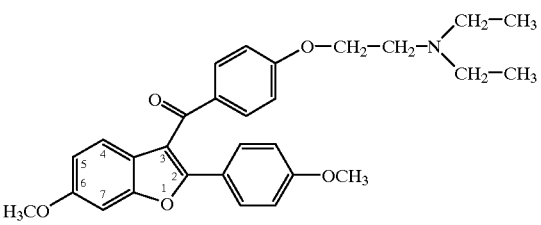

The title compound was prepared by reacting the compound of Preparation 4a supra, 2-(4-methoxyphenyl)-3-(4-hydroxybenzoyl)-6-methoxybenzofuran (10 g, 26.7 mmol) which is dissolved in 200 ml of N,N-dimethylformamide with an equimolar amount of 2-(N,N-diethylamino)ethyl chloride (6.4 g, 32 mmol) and potassium carbonate (11.06 g, 80.2 mmol). The mixture was heated to 100° C. and was maintained at that temperature for about two hours. The reaction mixture was then cooled to room temperature and maintained at this temperature overnight while stirring.

The solvents were then removed by evaporation and the residue was extracted from water with ethyl acetate and washed twice with a saturated sodium chloride solution. The organic phase was dried over sodium sufate and the solvents were removed in vacuo. The material was crystallized from hexane and recrystallized in methanol.

NMR, IR, MS. Analysis for $C_{29}H_{31}NO_5$: Theory: C, 73.55; H, 6.60; N, 2.96. Found: C, 73.29; H, 6.50; N, 2.84.

EXAMPLE 23

Synthesis of 2-(4-hydroxyphenyl)-3-[4-[2-(diethylamino)ethoxy]benzoyl]-6-hydroxybenzofuran hydrochloride

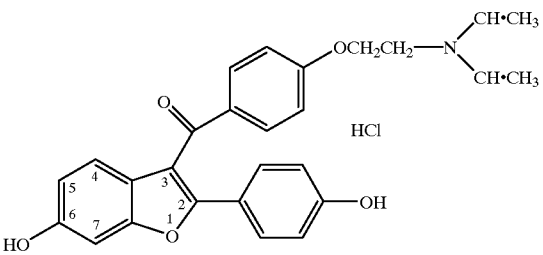

The title compound was prepared essentially as described in Example 19, supra, except that the compound of Example 5, 2-(4-methoxyphenyl)-3-[4-[2-(diethylamino)ethoxy] benzoyl]-6-methoxybenzofuran, was used as the starting material to be demethylated.

NMR, IR, MS. Analysis for $C_{27}H_{28}NO_5Cl$: Theory: C, 67.29; H, 5.86; N, 2.91. Found: C, 67.54; H, 5.64; N, 2.92.

EXAMPLE 24

Synthesis of 2-(4-methoxyphenyl)-3-[4-[2-(diisopropylamino)ethoxy]benzoyl]-6-methoxybenzofuran

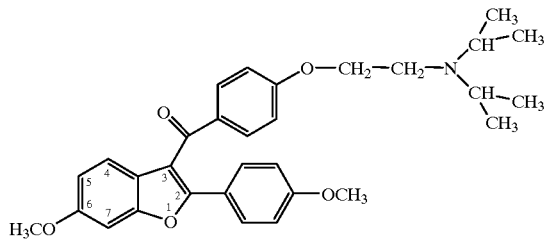

The title compound was prepared by reacting the compound of Preparation 4a supra, 2-(4-methoxyphenyl)-3-(4-hydroxybenzoyl)-6-methoxybenzofuran (10 g, 26.7 mmol) which is dissolved in 200 ml of N,N-dimethylformamide with 2-(N,N-diisopropylamino)ethyl chloride (6.4 g, 32 mmol) and potassium carbonate (11.06 g, 80.2 mmol). The mixture was heated to 100° C. and was maintained at that temperature for about two hours. The reaction mixture was then cooled to room temperature and maintained at this temperature overnight while stirring.

The solvents were then removed by evaporation and the residue was extracted from water with ethyl acetate and washed twice with a saturated sodium chloride solution. The organic phase was dried over sodium sufate and the solvents were removed in vacuo. The material was crystallized from hexane and recrystallized in methanol.

NMR, IR, MS. Analysis for $C_{33}H_{39}NO_5$: Theory: C, 74.83; H, 7.42; N, 2.64. Found: C, 74.68; H, 7.14; N, 2.76.

EXAMPLE 25

Synthesis of 2-(4-hydroxyphenyl)-3-[4-[2-(diisopropylamino)ethoxy]benzoyl]-6-hydroxybenzofuran hydrochloride

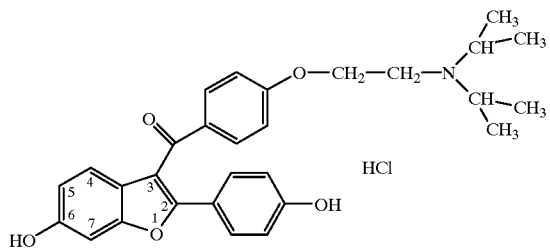

The title compound was prepared essentially as described in Example 19, supra, except that the compound of Example 24, 2-(4-methoxyphenyl)-3-[4-[2-(diisopropylamino)ethoxy]benzoyl]-6-methoxybenzofuran, was used as the starting material to be demethylated.

NMR, IR, MS. Analysis for $C_{29}H_{32}NO_5Cl$: Theory: C, 68.29; H, 6.32; N, 2.75. Found: C, 68.53; H, 6.49; N, 2.74.

EXAMPLE 26

Synthesis of 2-(4-methoxyphenyl)-3-[4-[2-(dimethylamino)ethoxy]benzoyl]-6-methoxybenzofuran

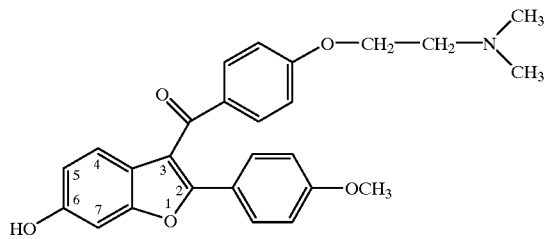

The title compound was prepared essentially as described in Example 24, supra, except that 2-(N,N-dimethylamino)ethyl chloride was reacted with 2-(4-methoxyphenyl)-3-(4-hydroxybenzoyl)-6-methoxybenzofuran instead of the 2-(N,N-diisopropylamino)ethyl chloride employed in that example.

NMR, IR, MS. Analysis for $C_{27}H_{27}NO_5$: Theory: C, 72.79; H, 6.11; N, 3.14. Found: C, 72.51; H, 6.27; N, 3.10.

EXAMPLE 27

Synthesis of 2-(4-hydroxyphenyl)-3-[4-[2-(dimethylamino)ethoxy]benzoyl]-6-hydroxybenzofuran

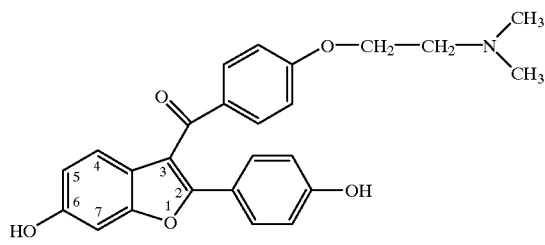

The title compound was prepared essentially as described in Example 19, supra, except that the compound of Example 26, 2-(4-methoxyphenyl)-3-[4-[2-(dimethylamino)ethoxy]benzoyl]-6-methoxybenzofuran, was used as the starting material to be demethylated.

NMR, IR, MS. Analysis for $C_{25}H_{23}NO_5$: Theory: C, 71.93; H, 5.55; N, 3.36. Found: C, 70.69; H, 5.51; N, 3.16.

EXAMPLE 28

Synthesis of 2-(4-methoxyphenyl)-3-[4-[2-(hexamethyleneimin-1-yl)ethoxy]benzoyl]-6-methoxybenzofuran

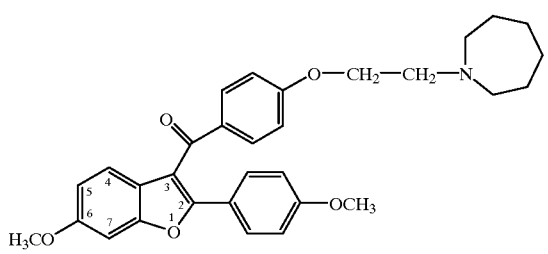

The title compound was prepared essentially as described in Example 24, supra, except that 2-(hexamethyleneimin-1-yl)ethyl chloride was reacted with 2-(4-methoxyphenyl)-3-(4-hydroxybenzoyl)-6-methoxybenzofuran instead of the 2-(N,N-diisopropylamino)ethyl chloride employed in that example.

NMR, IR, MS. Analysis for $C_{31}H_{33}NO_5$: Theory: C, 74.53; H, 6.66; N, 2.80. Found: C, 74.69; H, 6.70; N, 2.75.

EXAMPLE 29

Synthesis of 2-(4-hydroxyphenyl)-3-[4-[2-(hexamethyleneimin-1-yl)ethoxy]benzoyl]-6-hydroxybenzofuran hydrochloride

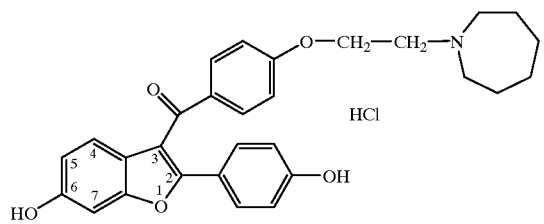

The title compound was prepared essentially as described in Example 19, supra, except that the compound of Example 28, 2-(4-methoxyphenyl)-3-[4-[2-(hexamethyleneimin-1-yl)ethoxy]benzoyl]-6-methoxybenzofuran, was used as the starting material to be demethylated.

NMR, IR, MS Analysis for $C_{29}H_{30}ClNO_5$: Theory: C, 68.57; H, 5.95; N, 2.76. Found: C, 67.28; H, 6.13; N, 2.66.

EXAMPLE 30

Synthesis of 2-(4-hydroxyphenyl)-3-[4-[2-(piperidin-1-yl)ethoxy]benzoyl]-6-hydroxybenzofuran hydrochloride

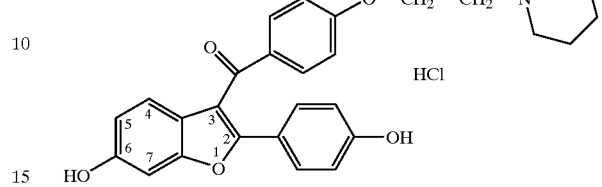

The title compound was prepared by dissolving the compound of Example 19, 2-(4-hydroxyphenyl)-3-[4-[2-(piperidin-1-yl)ethoxy]benzoyl]-6-hydroxybenzofuran, (3.1 g, 6.8 mmol) in 15 ml of methanol and treating with an excess of 3% hydrochloric acid in methanol. The volume was then reduced by boiling to 15 ml. Warm water (20 ml) was then added and the reaction mixture was further warmed to clarify. The reaction mixture was then filtered, followed by gradual cooling to 0° C., at which temperature the mixture was maintained for about one hour. The crystals, which had precipitated, were collected by filtration and washed with cold water. The pale yellow crystals were dried overnight, resulting in 2.82 g (84%) of the desired title product. mp 213–215° C.

NMR, IR, MS. Analysis for $C_{28}H_{28}NO_5Cl$: Theory: C, 68.08; H, 5.71; N, 2.84; O, 16.19. Found: C, 67.86; H, 5.51; N, 2.88; O, 15.93.

EXAMPLE 31

Synthesis of 2-(4-hydroxyphenyl)-3-[4-[2-(piperidin-1-yl)ethoxy]benzoyl]benzofuran hydrochloride

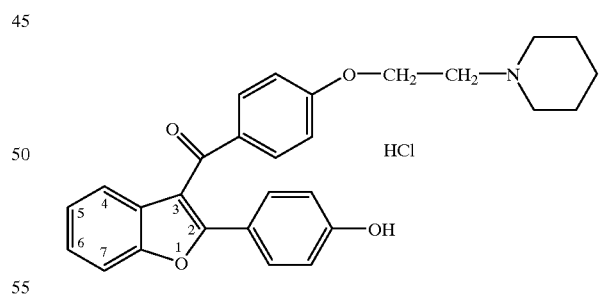

The 2-(4-hydroxyphenyl)-3-[4-[2-(piperidin-1-yl)ethoxy]benzoyl]benzofuran was prepared essentially as described in Example 19, except that phenol was used as a starting material in the synthesis described in Preparation 2a instead of 3-methoxy phenol. The hydrochloride salt of this substituted benzofuran was prepared essentially as described in Example 30, supra.

NMR, IR, MS. Analysis for $C_{28}H_{28}NO_4Cl$: Theory: C, 70.36; H, 5.91; N, 2.93. Found: C, 70.46; H, 5.84; N, 2.84.

EXAMPLE 32

Synthesis of 2-phenyl-3-[4-[2-(piperidin-1-yl)ethoxy]benzoyl]-6-hydroxybenzofuran hydrochloride

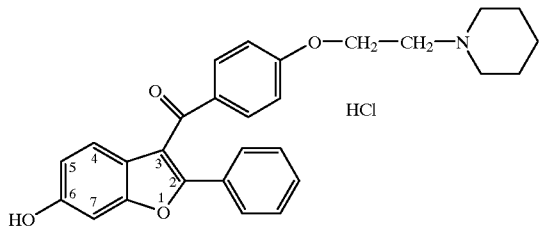

The 2-phenyl-3-[4-[2-(piperidin-1-yl)ethoxy]benzoyl]-6-hydroxybenzofuran was prepared essentially as described in Example 19, except that phenacylbromide (also known as α-bromoacetophenone) was used as a starting material in the synthesis described in Preparation 1a instead of 4-methoxyphenacylbromide. The hydrochloride salt of this substituted benzofuran was prepared essentially as described in Example 30, supra.

NMR, IR, MS. Analysis for $C_{28}H_{28}NO_4Cl$: Theory: C, 70.36; H, 5.90; N, 2.93. Found: C, 70.39; H, 6.01; N, 2.91.

EXAMPLE 33

Synthesis of 1-ethyl-2-(4-methoxyphenyl)-3-(4-(2-(piperidin-1-yl)ethoxy]benzoyl]-6-hydroxyindole hydrochloride salt

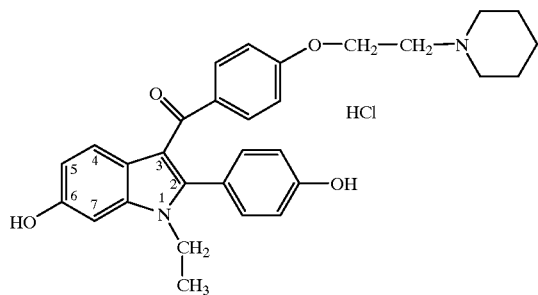

To 814 milliliters of concentrated hydrochloric acid in a 3 liter, 3-neck round bottom flask which had been cooled to 0° C. was added 3-methoxyaniline (99.26 g, 0.806 mole). Sodium nitrate (55.61 g, 0.806 mole), dissolved in 249 milliliters of water, was added dropwise to the 3-methoxyaniline solution at such a rate that the reaction temperature never exceeded 0° C. This mixture was then stirred for about 90 minutes.

Stannous chloride (545.57 g, 2.418 mol), dissolved in 497 milliliters of concentrated hydrochloric acid, was added dropwise to the reaction mixture at such a rate that the reaction temperature never exceeded 5° C. This mixture was then stirred for about two hours after the addition of the stannous chloride was completed, resulting in the formation of a thick, beige, chalky emulsion. The solid was removed by filtration, stored overnight in one liter of water and then basified with a 25% solution of sodium hydroxide. This aqueous solution was extracted with diethyl ether (3×1 liter) and then dried over sodium sulfate. The solvents were removed in vacuo, resulting in a brown oil of 3-methoxyphenylhydrazine (76.3 g, 69% yield).

The 3-methoxyphenylhydrazine (76.3 g, 0.552 mole) prepared supra, was dissolved in 400 milliliters of ethanol. To this mixture was added p-methoxyacetophenone (82.80 g, 0.552 mole) followed by the addition of about 6 drops of hydrochloric acid. This mixture was then stirred for about seven hours under a nitrogen atmosphere, followed by storage at 4° C. for about 3 days.

The white solid was then removed from the suspension by filtration under vacuum and then dried in vacuo, resulting in 135.2 grams (91% yield) of [(3-methoxyphenyl)hydrazono]-1-methyl-4-methoxybenzylidene of the following formula as a pale gray solid.

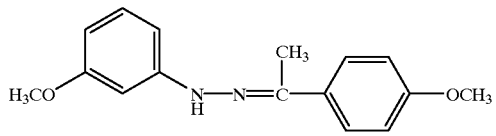

Zinc chloride (66.5 g, 0.49 mole) was added to a 3-neck round bottom flask under a nitrogen atmosphere. The flask and its contents were then heated to 200° C. at which time the hydrazone (26.4 g, 0.098 mole) prepared supra was added. The mixture was stirred for about 17 minutes, resulting in the formation of a brown tar and the evolution of some gas. The brown tar was then poured into two liters of 0.075 N hydrochloric acid and this mixture was stirred for about 48 hours, resulting in the formation of a yellow solid.

The solids were removed by filtration and were then recrystallized from methanol. The solids were again removed by filtration and the solvents were removed in vacuo to yield the desired 2-(4-methoxyphenyl)-6-methoxyindole (5.50 g, 22% yield) as a white crystalline product.

The 2-(4-methoxyphenyl)-6-methoxyindole (2.0 g, 8 mmol) was dissolved in 40 milliliters of N,N-dimethylformamide. This solution was added dropwise to a solution of sodium hydride (0.48 g, 12 mmol) in ten milliliters of N,N-dimethylformamide. This reaction mixture was then stirred at room temperature for 1 hour at which time a solution of ethyl iodide (1.9 g, 12 mmol) in N,N-dimethylformamide (10 ml) was added dropwise over five minutes. This mixture was then stirred at room temperature for about two hours.

The reaction was quenched by the addition of methanol. The volume of the solvents was reduced by vacuum, leaving a brown oil. This oil was diluted with chloroform, washed with 5 N sodium hydroxide (3×75 ml), followed by washing with water (2×200 ml). The organic layer was dried over sodium sulfate and the solvents were removed in vacuo leaving 2.3 g of the desired intermediate 1-ethyl-2-(4-methoxyphenyl)-6-methoxyindole as white crystals.

The preceding intermediate was acylated at the 3-position by first placing N,N-dimethyl-4-methoxybenzamide (1.43 g, 8 mmol), in a 100 ml flask cooled to 0° C. To this was then added phosphorous oxychloride (6.1 g, 40 mmol) dropwise at such a rate that the reaction temperature never exceeded 20° C. The reaction mixture was allowed to warm to room temperature and was stirred for about 30 minutes. The reaction mixture was then cooled to 0° C. and the 1-ethyl-2-(4-methoxyphenyl)-6-methoxyindole (1.5 g, 5.33 mmol) prepared supra, was added and the reaction mixture was then heated to 75° C. and maintained at this temperature for about three hours.

After this incubation, the reaction mixture was poured over ice and diluted with water. The layers were separated and the organic phase was washed with water (150 ml). The organic layer was dried over sodium sulfate and the solvents were removed in vacuo to yield a dark brown/black oil. This oil was taken up in 50 milliliters of methanol and cooled to 0° C. This solution was then basified by the dropwise addition of 2N sodium hydroxide (50 ml). The mixture was then heated to reflux for about 5 minutes, then cooled overnight at 4° C.

The precipitate was then removed by filtration and recrystallized from methanol, resulting in 2.21 grams (86% yield) of the intermediate 1-ethyl-2-(4-methoxyphenyl)-3-(4-methoxybenzoyl)-6-methoxyindole as a yellow precipitate.

The above intermediate (2.1 g, 5.05 mmol) was then admixed with sodium thioethoxide (0.85 g, 10.11 mmol) in N,N-dimethylformamide (12 ml). The reaction mixture was then heated to 85° C. and maintained at this temperature for about six hours. The desired intermediate 1-ethyl-2-(4-methoxyphenyl)-3-(4-hydroxybenzoyl)-6-methoxyindole was then recrystallized from ethyl acetate.

This intermediate (1.5 g, 3.74 mmol) was then reacted with 2-(piperidin-1-yl)ethyl chloride hydrochloride (1.38 g, 7.5 mmol) in N,N-dimethylformamide (60 ml) in the presence of cesium carbonate (3.26 g, 10 mmol). This admixture was heated to 80° C. and maintained at this temperature for about two hours.

The precipitate was collected by filtration and then taken up in chloroform, and washed with 2 N sodium hydroxide (3×125 ml) and water (3×100 ml). The organic fraction was then dried over sodium sulfate and the solvents were removed in vacuo to yield 2.05 grams (95% yield) of 1-ethyl-2-(4-methoxyphenyl)-3-[4-[2-(piperidin-1-yl)ethoxy]benzoyl]-6-methoxyindole as a gray foam.

This intermediate (1.0 g, 1.82 mmol) was dissolved in dichloromethane (10 ml) and cooled to 0° C. To this mixture was then added the Lewis acid aluminum chloride (1.2 g, 9 mmol) and the reaction mixture was then stirred for five minutes. Ethanol (3 ml) were then added and the reaction mixture was stirred on ice for about 15 minutes. The temperature of the reaction mixture was slowly raised to reflux and maintained at reflux for about 1.5 hours.

The reaction mixture was then cooled to 0° C. and this temperature was maintained as tetrahydrofuran (5 ml) was added. To this mixture was then added 20% hydrochloric acid in water (5 ml) and the reaction mixture was cooled back to 0° C. at which time five milliliters of water was then added, resulting in the formation of a yellow gum. This suspension was then placed at −40° C. and kept at this temperature for about 48 hours, after which time a grayish material was removed from the mixture by filtration. Thin layer chromatography confirmed this precipitate as the desired title product.

NMR, MS. Analysis for $C_{30}H_{33}ClN_2O_4$: Theory: C, 69.15; H, 6.38; N, 5.38. Found: C, 69.09; H, 6.43; N, 5.53.

EXAMPLE 34

Synthesis of 2-(4-hydroxyphenyl)-3-[4-[3-(piperidin-1-yl)propoxy]benzoyl]-6-hydroxybenzo[b]thiophene hydrochloride

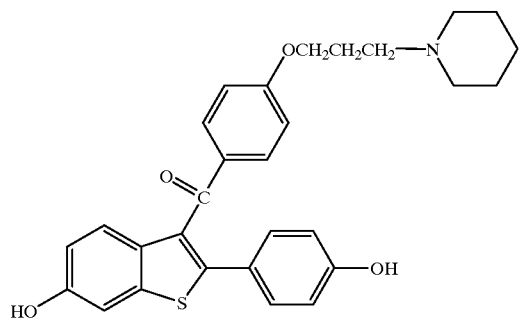

The title compound was prepared essentially as described in U.S. Pat. No. 4,380,635, which is herein incorporated by reference with the exception that 4-[3-(piperidin-1-yl)propoxy]benzoyl chloride was used to acylate the substituted benzo[b]thiophene rather than the 4-[2-(piperidin-1-yl)ethoxy]benzoyl chloride employed therein.

EXAMPLE 35

Synthesis of 2-phenyl-3-[4-[2-(pyrrolidin-1-yl)ethoxy]benzoyl]benzo[b]thiophene

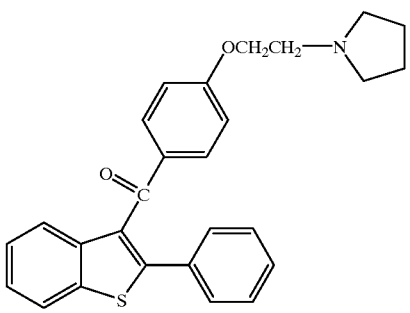

The title compound was prepared as described in U.S. Pat. No. 4,133,814, which is herein incorporated by reference.

EXAMPLE 36

Synthesis of 2-phenyl-3-[4-[2-(pyrrolidin-1-yl)ethoxy]benzoyl]-6-methoxybenzo[b]thiophene citrate

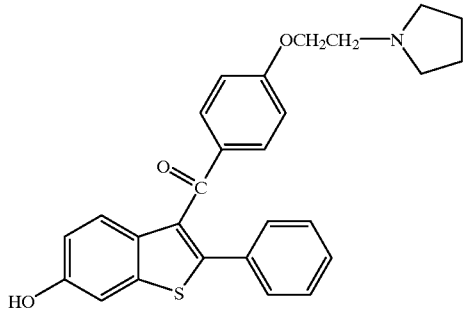

The title compound was prepared as described in U.S. Pat. No. 4,133,814, which is herein incorporated by reference.

EXAMPLE 37

Synthesis of 2-(4-methoxyphenyl)-3-[4-[2-(pyrrolidin-1-yl)ethoxy]benzoyl]benzo[b]thiophene citrate

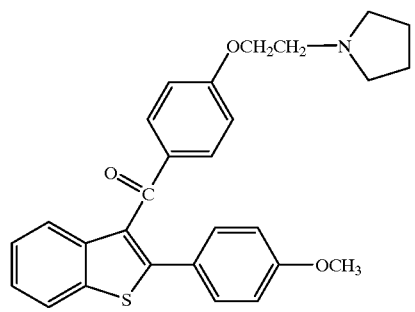

The title compound was prepared as described in U.S. Pat. No. 4,133,814, which is herein incorporated by reference.

EXAMPLE 38

Synthesis of 2-(4-ethoxyphenyl)-3-[4-[2-(pyrrolidin-1-yl)ethoxy]benzoyl]-6-methoxybenzo[b]thiophene citrate

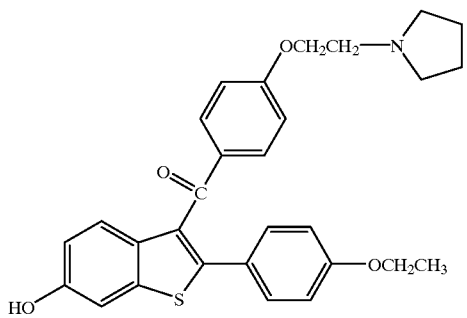

The title compound was prepared as described in U.S. Pat. No. 4,133,814, which is herein incorporated by reference.

EXAMPLE 39

Synthesis of 2-(4-acetoxyphenyl)-3-[4-[2-(pyrrolidin-1-yl)ethoxy]benzoyl]benzo[b]thiophene citrate

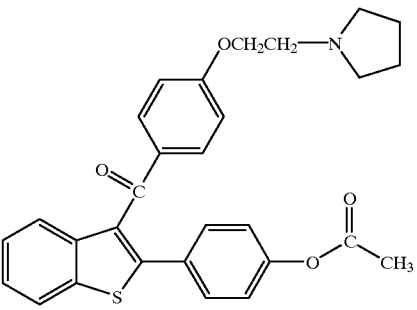

The title compound was prepared as described in U.S. Pat. No. 4,133,814, which is herein incorporated by reference.

EXAMPLE 40

Synthesis of 2-phenyl-3-[4-[2-(piperidin-1-yl)ethoxy]benzoyl]benzo[b]thiophene

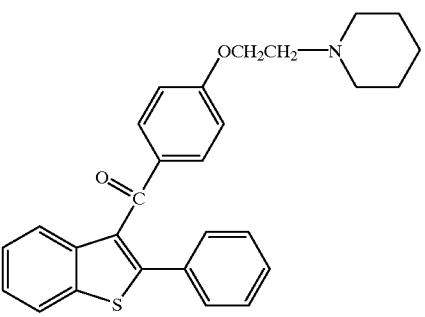

The title compound was prepared as described in U.S. Pat. No. 4,133,814, which is herein incorporated by reference.

EXAMPLE 41

Synthesis of 2-phenyl-3-[4-[2-(piperidin-1-yl)ethoxy]benzoyl]-6-methoxybenzo[b]thiophene citrate

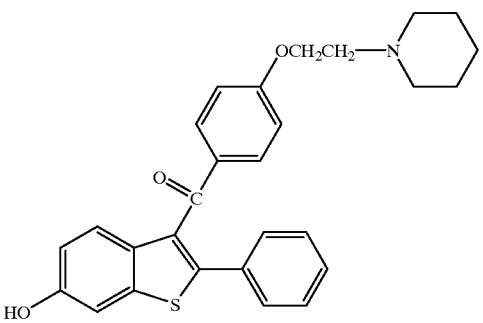

The title compound was prepared as described in U.S. Pat. No. 4,133,814, which is herein incorporated by reference.

EXAMPLE 42

Synthesis of 2-(4-methoxyphenyl)-3-[4-[2-(piperidin-1-yl)ethoxy]benzoyl]benzo[b]thiophene citrate

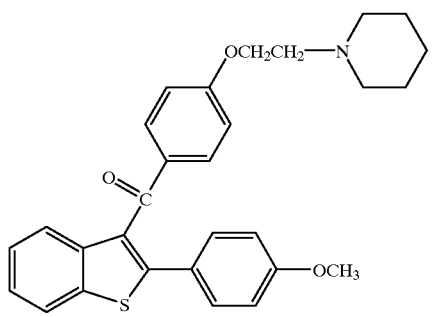

The title compound was prepared as described in U.S. Pat. No. 4,133,814, which is herein incorporated by reference.

EXAMPLE 43

Synthesis of 2-(4-ethoxyphenyl)-3-[4-[2-(piperidin-1-yl)ethoxy]benzoyl]-6-methoxybenzo[b]thiophene citrate

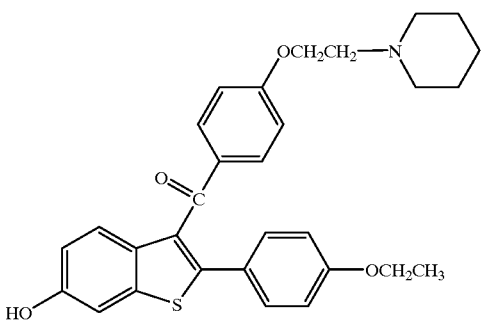

The title compound was prepared as described in U.S. Pat. No. 4,133,814, which is herein incorporated by reference.

EXAMPLE 44

Synthesis of 2-(4-acetoxyphenyl)-3-[4-[2-(piperidin-1-yl)ethoxy]benzoyl]benzo[b]thiophene citrate

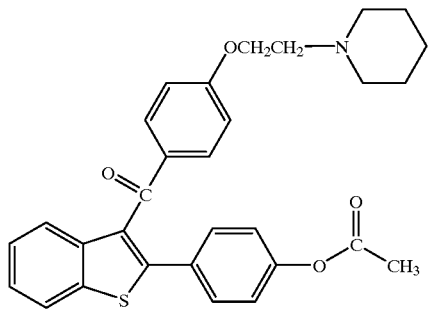

The title compound was prepared as described in U.S. Pat. No. 4,133,814, which is herein incorporated by reference.

EXAMPLE 45

Synthesis of 2-(4-pentanoylphenyl)-3-[4-[2-(piperidin-1-yl)ethoxy]benzoyl]benzo[b]thiophene citrate

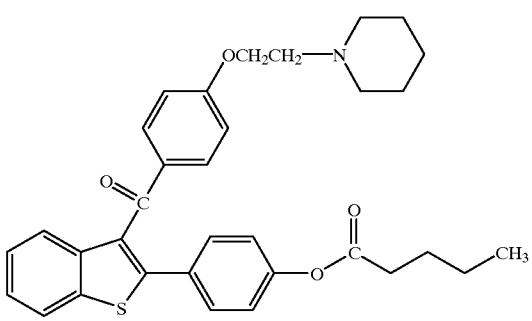

The title compound, also known as 2-(4-valerylphenyl)-3-[4-[2-(piperidin-1-yl)ethoxy]benzoyl]benzo[b]thiophene citrate, was prepared as described in U.S. Pat. No. 4,133,814, which is herein incorporated by reference.

EXAMPLE 46

Synthesis of 2-(4-chlorophenyl)-3-[4-[2-(piperidin-1-yl)ethoxy]benzoyl]benzo[b]thiophene citrate

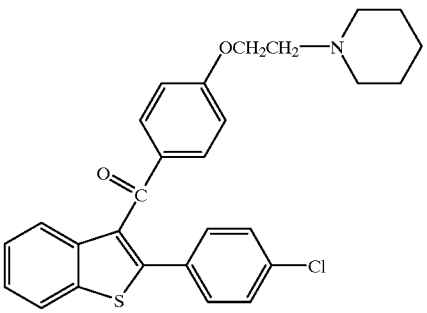

The title compound was prepared as described in U.S. Pat. No. 4,133,814, which is herein incorporated by reference.

EXAMPLE 47

Synthesis of 2-phenyl-3-[4-[2-(hexamethyleneimin-1-yl)ethoxy]benzoyl]benzo[b]thiophene

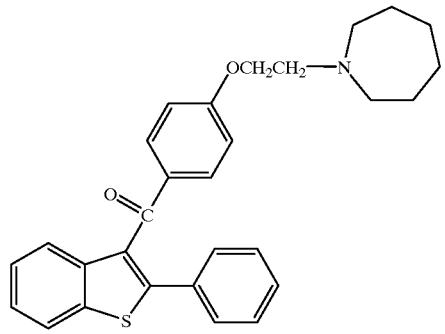

The title compound was prepared as described in U.S. Pat. No. 4,133,814, which is herein incorporated by reference.

EXAMPLE 48

Synthesis of 2-phenyl-3-[4-[2-(hexamethyleneimin-1-yl)ethoxy]benzoyl]-6-methoxybenzo[b]thiophene citrate

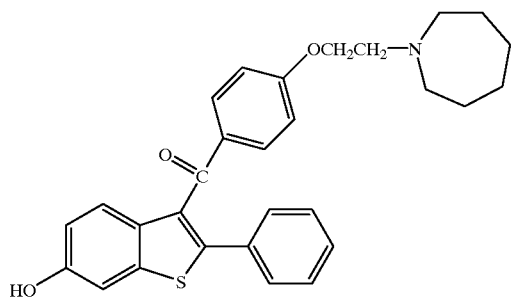

The title compound was prepared as described in U.S. Pat. No. 4,133,814, which is herein incorporated by reference.

EXAMPLE 49

Synthesis of 2-(4-methoxyphenyl)-3-[4-[2-(hexamethyleneimin-1-yl)ethoxy]benzoyl]benzo[b]thiophene citrate

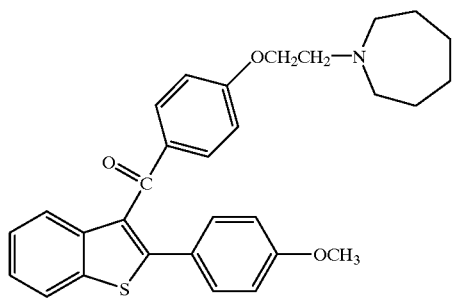

The title compound was prepared as described in U.S. Pat. No. 4,133,814, which is herein incorporated by reference.

EXAMPLE 50

Synthesis of 2-(4-ethoxyphenyl)-3-[4-[2-(hexamethyleneimin-1-yl)ethoxy]benzoyl]-6-methoxybenzo[b]thiophene citrate

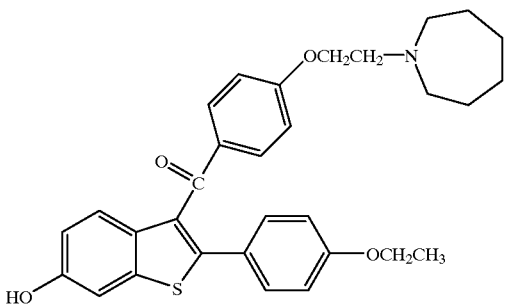

The title compound was prepared as described in U.S. Pat. No. 4,133,814, which is herein incorporated by reference.

EXAMPLE 51

Synthesis of 2-(4-acetoxyphenyl)-3-[4-[2-(hexamethyleneimin-1-yl)ethoxy]benzoyl]benzo[b]thiophene citrate

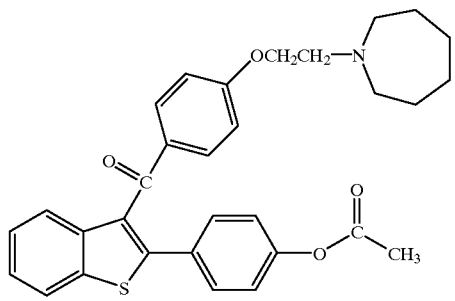

The title compound was prepared as described in U.S. Pat. No. 4,133,814, which is herein incorporated by reference.

EXAMPLE 52

Synthesis of 2-(4-pentanoylphenyl)-3-[4-[2-(hexamethyleneimin-1-yl)ethoxy]benzoyl]benzo[b]thiophene citrate

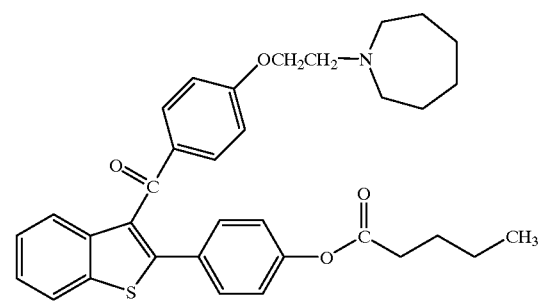

The title compound, also known as 2-(4-valerylphenyl)-3-[4-[2-(hexamethyleneimin-1-yl)ethoxy]benzoyl]benzo[b]

EXAMPLE 53

Synthesis of 2-(4-chlorophenyl)-3-[4-[2-(hexamethyleneimin-1-yl)ethoxy]benzoyl]benzo[b]thiophene citrate

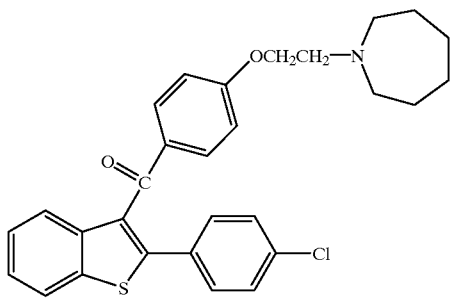

The title compound was prepared as described in U.S. Pat. No. 4,133,814, which is herein incorporated by reference.

EXAMPLE 54

Synthesis of 2-(4-chlorophenyl)-3-[4-[2-(piperidin-1-yl)ethoxy]benzoyl]benzo[b]thiophene-1-oxide

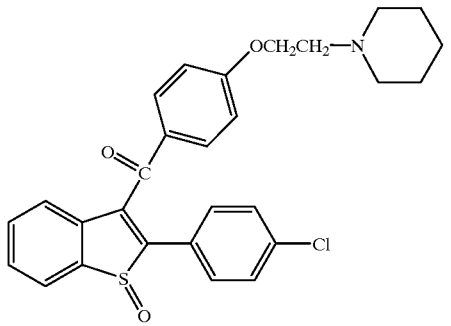

The title compound was prepared as described in U.S. Pat. No. 4,133,814, which is herein incorporated by reference.

EXAMPLE 55

Synthesis of 2-(4-chlorophenyl)-3-[4-[2-(pyrrolidin-1-yl)ethoxy]benzoyl]benzo[b]thiophene-1-oxide

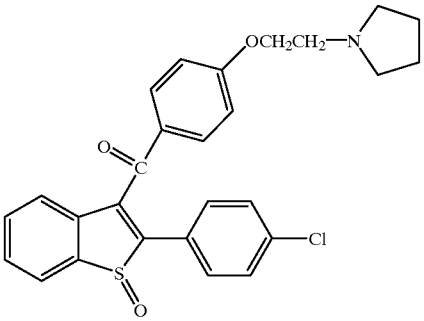

The title compound was prepared as described in U.S. Pat. No. 4,133,814, which is herein incorporated by reference.

Those compounds employed in the methods of the instant invention in which R or $R^1$ are —$OSO_2$—($C_1$–$C_{10}$ alkyl) or

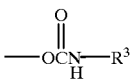

were made essentially as described in European Patent Application 617,030, published Sep. 28, 1994. Those compounds employed in the methods of the instant invention wherein at least one of $R^1$ and R is —$OSO_2$—($C_1$–$C_{10}$ alkyl) were generally prepared by reacting a compound of Formula II

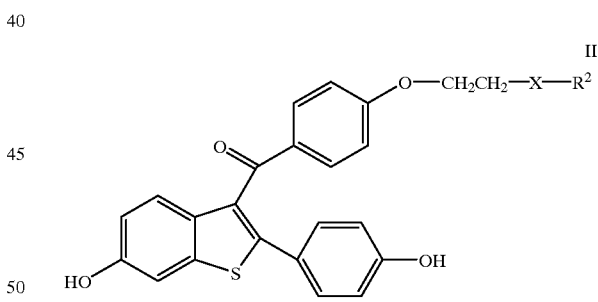

with an alkyl sulfonyl of Formula IIa

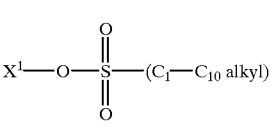

where $X^1$ is a leaving group, preferably a chloro or bromo group. This reaction is usually performed in a basic environment in the presence of a coupling catalyst such as 4-dimethylaminopyridine (DMAP). Most preferred solvents include the lower alkyl amines, especially triethylamine. While this thioester formation reaction may be performed at equal molar ratios of the two reactants, it is usually preferred to employ a 2–3 molar excess of the alkyl sulfonyl compound so as to complete the reaction.

The following examples will illustrate preparation of these compounds of this invention but are not intended to limit it in any way.

EXAMPLE 56

Preparation of [6-(n-butylsulfonoyl)-2-[4-(n-butylsulfonoyl)phenyl]benzo[b]thien-3-yl][4-[2-(1-piperidinyl)ethoxy]-phenyl]methanone

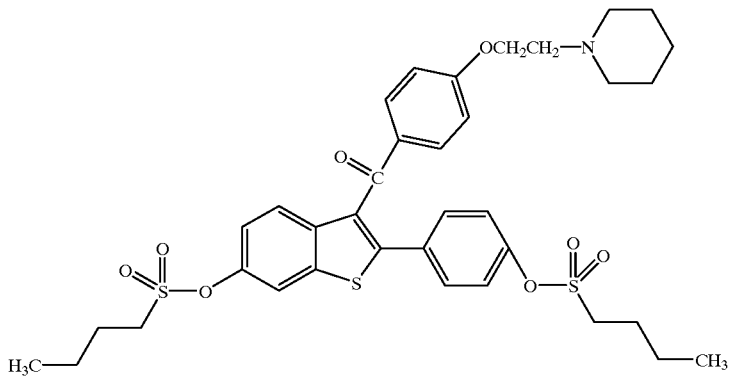

In dry tetrahydrofuran (250 ml) [6-hydroxy-2-(4-hydroxyphenyl)-benzo[b]thien-3-yl]-[4-[2-(1-piperidinyl)ethoxyphenyl]-methanone, hydrochloride (5.1 g, 10 mmol) was suspended and 7.1 g (70 mmol) of triethylamine was added. The reaction mixture was cooled to 0° C. in an ice bath and 10 mg of 4-dimethylaminopyridine (DMAP) was added, followed by the slow addition of n-butylsulfonyl chloride (4.7 g, 30 mmol). The reaction mixture was placed under a nitrogen atmosphere and allowed to warm slowly to room temperature and continued for 72 hours. The reaction mixture was filtered and evaporated to an oil. The oily residue was dissolved in chloroform and chromatographed on a silica gel column and eluted with a linear gradient of chloroform to chloroform-methanol (19:1; V:V). The desired fractions were combined and evaporated to dryness to afford 5.60 g of the title compound as a tan amorphous powder.

$C_{36}H_{43}NO_8S_3$; MS (FD) m/e=714 (M+1); NMR was consistent with the proposed structure.

EXAMPLE 57

Preparation of [6-(n-butylsulfonoyl)-2-[4-(n-butylsulfonoyl)phenyl]benzo[b]thien-3-yl][4-[2-(1-piperidinyl)ethoxy]-phenyl]methanone, Hydrochloride

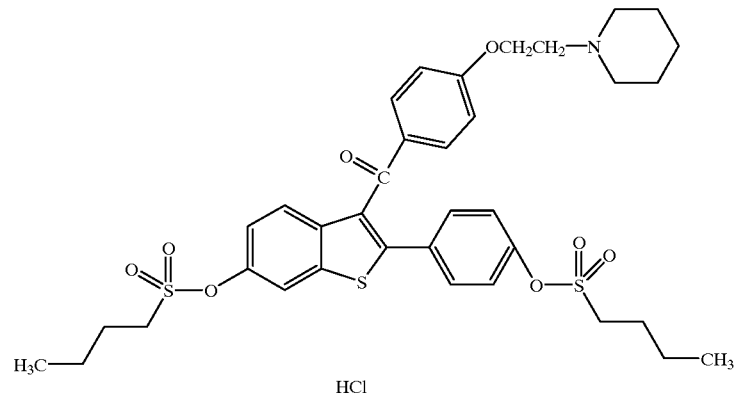

The compound of Example 1, [6-(n-Butylsulfonoyl)-2-[4-(n-butylsulfonoyl)phenyl]-benzo[b]thien-3-yl][4-[2-(1-piperidinyl)ethoxy]-phenyl]methanone (5.4 g) was dissolved in ethyl acetate (EtOAc) and a solution of ether, saturated with hydrochloric acid, was added until no more precipitate was formed. The liquid was decanted off and the solid was triturated with ether. The title compound was crystallized from hot ethyl acetate to afford 3.74 g, as a white powder.

$C_{36}H_{43}NO_8S_3$—HCl;

| Elemental Analysis: | C | H | N |
|---|---|---|---|
| Calculated: | 57.7 | 5.88 | 1.87 |
| Found: | 57.75 | 5.93 | 1.93 |

NMR was consistent with the proposed structure.

EXAMPLE 58

Preparation of [6-(n-pentylsulfonoyl)-2-[4-(n-pentylsulfonoyl)phenyl]benzo[b]thien-3-yl][4-[2-(1-piperidinyl)ethoxy]-phenyl]methanone volatiles were removed in vacuo. The resulting material was dissolved in a small amount of chloroform and chromatographed (HPLC) on a silica gel column eluted with a linear gradient starting with chloroform and ending with chloroform-methanol (19:1 v/v). The desired fractions were determined by thin layer chromatography, combined and evaporated down to afford 3.82 g of the title compound as thick oil.

$C_{38}H_{47}NO_8S_3$; NMR: consistent with the proposed structure; MS: (FD) m/e=743 (M+2);

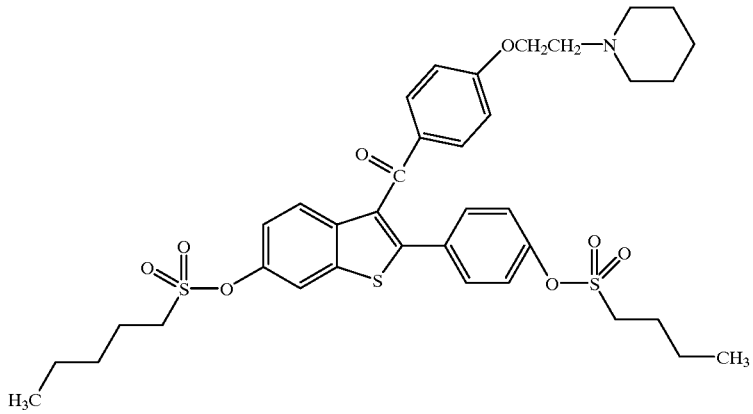

In dry tetrahydrofuran (100 ml) of [6-hydroxy-2-(4-hydroxyphenyl)-benzo[b]thien-3-yl]-[4-[2-(1-piperidinyl)ethoxy]phenyl-]methanone, hydrochloride (3 g, 5.9 mmol) was suspended and 10 mg of DMAP was added followed by 3 g (30 mmol) of triethylamine. The reaction mixture was stirred at room temperature and under a nitrogen blanket for about 20 minutes. n-Pentyl sulfonyl chloride (2.5 g, 14.7 mmol) was dissolved in 25 ml of tetrahydrofuran and slowly added to the stirring reaction mixture. The reaction was allowed to proceed at room temperature and under nitrogen for eighteen hours. The reaction mixture was filtered and the

| Elemental Analysis: | C | H | N |
|---|---|---|---|
| Calculated: | 61.51 | 6.39 | 1.89 |
| Found: | 57.63 | 6.44 | 1.50 |

EXAMPLE 59

Preparation of [6-(n-pentylsulfonoyl)-2-[4-(n-pentylsulfonoyl)phenyl]benzo[b]thien-3-yl][4-[2-(1-piperidinyl)ethoxy]-phenyl]methanone, Hydrochloride

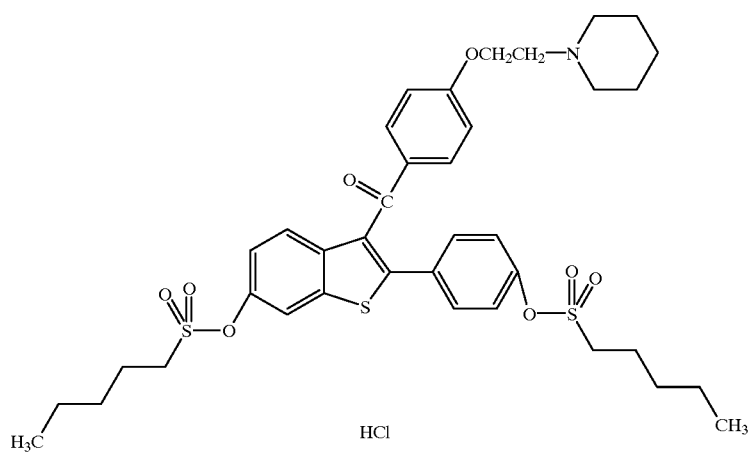

[6-(n-Pentylsulfonoyl)-2-[4-(n-pentylsulfonoyl)phenyl] benzo[b]thien-3-yl][4-[2-(1-piperidinyl)ethoxy]-phenyl] methanone (3.7 g) was dissolved in 25 ml of ethyl acetate and a solution of hydrochloric acid saturated diethyl ether was added. A precipitate formed and the liquid decanted off. The gummy solid was triturated with diethyl ether and dried in vacuo at room temperature to afford 2.12 g of the title compound as a white amorphous and hygroscopic solid.

$C_{38}H_{47}NO_8S_3$ HCl; NMR: consistent with the proposed structure;

| Elemental Analysis: | C | H | N |
|---|---|---|---|
| Calculated: | 58.63 | 6.22 | 1.80 |
| Found: | 57.35 | 6.45 | 1.38 |

EXAMPLE 60

Preparation of [6-(n-hexylsulfonoyl)-2-[4-(n-hexylsulfonoyl)phenyl]benzo[b]thien-3-yl][4-[2-(1-piperidinyl)ethoxy]-phenyl]methanone $C_{40}H_{51}NO_8S_3$; NMR: consistent with the proposed structure; MS: (FD) m/e=771 (M+1);

| Elemental Analysis: | C | H | N |
|---|---|---|---|
| Calculated: | 62.39 | 6.68 | 1.82 |
| Found: | 62.33 | 6.62 | 2.03 |

EXAMPLE 61

Preparation of [6-(n-Hexylsulfonoyl)-2-[4-(n-hexylsulfonoyl)phenyl]benzo[b]thien-3-yl][4-[2-(1-piperidinyl)ethoxy]-phenyl]methanone, Hydrochloride

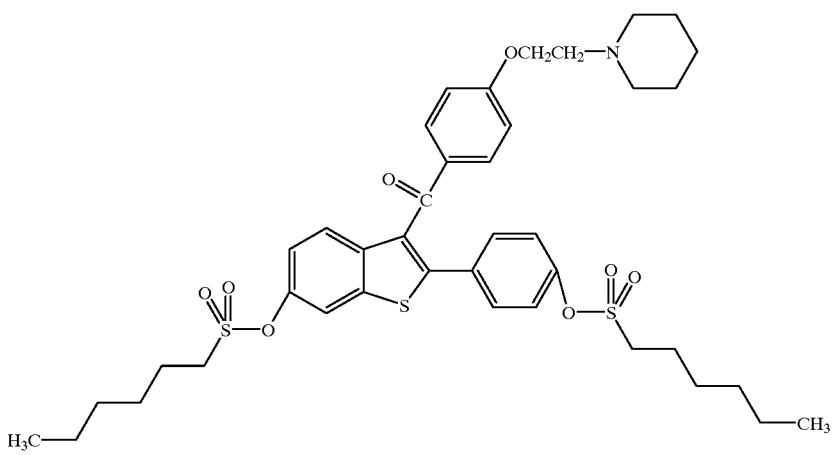

In dry tetrahydrofuran (250 ml) 3 g (5.9 mmol) of [6-hydroxy-2-(4-hydroxyphenyl)-benzo[b]thien-3-yl][4-[2-(1-piperidinyl)ethoxy]phenyl]-methanone hydrochloride was suspended and 10 mg of DMAP was added. Triethylamine (4 g, 40 mmol) was then added and the reaction mixture was stirred for 20 minutes at room temperature under a nitrogen blanket. n-Hexylsulfonyl chloride (3.6 g, 19.6 mmol) in 25 ml of tetrahydrofuran was slowly added to the reaction mixture. The reaction was allowed to proceed at room temperature and under nitrogen for 3 days. The reaction mixture was evaporated down in vacuo and resuspended in ethyl acetate and washed with water. The organic layer was dried by filtering it through anhydrous sodium sulfate and evaporated to a yellow oil. The oil was dissolved in chloroform and chromatographed (HPLC) on a silica gel column and eluted with a linear gradient starting with chloroform and ending with chloroform-methanol (19:1 v/v). The desired fractions were determined by thin layer chromatography, combined and evaporated down to afford 3.14 g of the title compound as a thick oil.

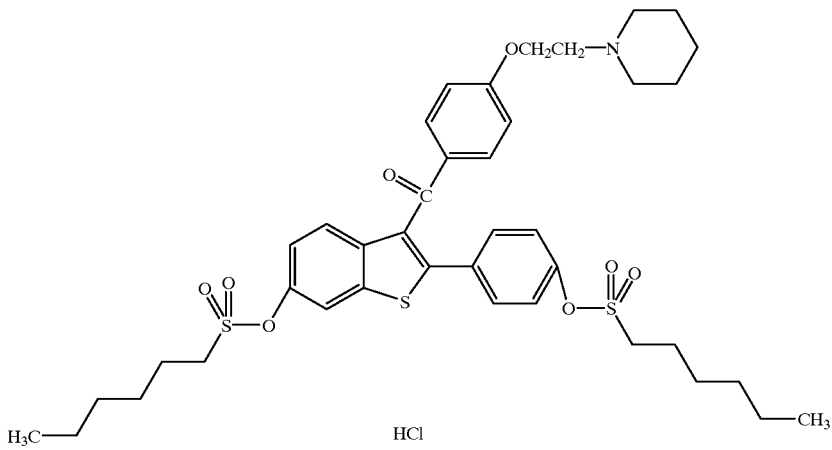

[6-(n-Hexylsulfonoyl)-2-[4-(n-hexylsulfonoyl)phenyl] benzo[b]thien-3-yl][4-[2-(1-piperidinyl)ethoxy]-phenyl] methanone (3 g) was dissolved in 20 ml of ethyl acetate and hydrochloric acid-saturated diethyl ether was added. No precipitate formed. The reaction mixture was evaporated to a thick oil and was triturated several times with diethyl ether and dried in vacuo at room temperature to afford 1.64 g of the title compound as a white amorphous and hygroscopic powder.

NMR: consistent with the proposed structure;

| Elemental Analysis: | C | H | N |
|---|---|---|---|
| Calculated: | 59.67 | 6.50 | 1.74 |
| Found: | 59.47 | 6.59 | 1.77 |

$C_{40}H_{51}NO_8S_3$—HCl.

EXAMPLE 62

Preparation of [6-(n-Butylsulfonoyl)-2-[4-(n-butylsulfonoyl)phenyl]benzo[b]thien-3-yl][4-[2-(1-piperidinyl)ethoxy]-phenyl]methanone, Citrate 2 g (2.8 mmol) of [6-(n-Butylsulfonoyl)-2-[4-(n-butylsulfonoyl)phenyl]benzo[b]thien-3-yl][4-[2-(1-piperidinyl)ethoxy]-phenyl]methanone was dissolved in 200 ml of acetone and 0.63 g (3 mmol) of citric acid was added. The reaction mixture remained at room temperature and under a nitrogen blanket for eighteen hours. The reaction mixture was evaporated in vacuo at 50° C. The reaction mixture was triturated several times with ether and dried at room temperature in vacuo to afford 2.35 g of the title compound as a white amorphous and hygroscopic powder.

| Elemental Analysis: | C | H | N |
|---|---|---|---|
| Calculated: | 55.68 | 5.67 | 1.55 |
| Found: | 55.39 | 5.60 | 1.60 |

NMR: consistent with the proposed structure.

EXAMPLE 63

Preparation of [6-(n-butylsulfonoyl)-2-[4-(n-butylsulfonoyl)phenyl]benzo[b]thien-3-yl][4-[3-(1-piperidinyl)propoxy]phenyl]methanone

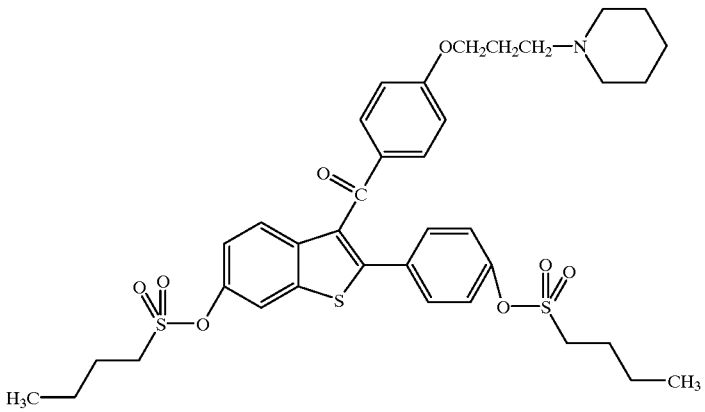

2.5 g (4.77 mmol) of [6-hydroxy-2-[4-hydroxyphenyl]benzo-[b]thien-3-yl][4-[3-(1-piperidinyl)propoxy]-phenyl]methanone hydrochloride was dissolved in 100 ml of tetrahydrofuran, 3.9 g (39 mmol) of triethylamine and 10 mg of DMAP were added. The reaction mixture was stirred for 15 minutes at room temperature and under a nitrogen blanket. 4 g (25.5 mmol) of n-butylsulfonyl chloride in 15 ml of tetrahydrofuran was slowly added. The reaction was allowed to proceed for eighteen hours at room temperature and under nitrogen. The reaction was quenched with the addition of 25 ml methanol and volume reduced in vacuo. The crude product was chromatographed on a silica gel column, eluted with chloroform-methanol (19:1 v/v). The desired fractions were determined by thin layer chromatography, combined, and evaporated to a tan oil.

EXAMPLE 64

Preparation of [6-(n-butylsulfonoyl)-2-[4-(n-butylsulfonoyl)phenyl]benzo[b]thien-3-yl][4-[3-(1-piperidinyl)propoxy]-phenyl]methanone, hydrochloride

[6-(n-Butylsulfonoyl)-2-[4-(n-butylsulfonoyl)phenyl]-benzo[b]thien-3-yl][4-[3-(1-piperidinyl)propoxy]-phenyl]methanone was dissolved in ethyl acetate-hexane and hydrogen chloride gas was bubbled in. The reaction mixture was evaporated down and chromatographed (HPLC) on a silica gel column eluted with chloroform and then with chloroform-methanol (19:1 v/v). The desired fractions were determined by thin layer chromatography and combined and evaporated down to a tan amorphous powder to afford 2.5 g of the title compound.

NMR: consistent with the proposed structure; MS: (FD) m/e=728 (M—HCl);

| Elemental Analysis: | C | H | N |
|---|---|---|---|
| Calculated: | 58.14 | 6.07 | 1.83 |
| Found: | 57.90 | 6.05 | 1.82 |

$C_{37}H_{46}NO_8S_3$—HCl.

EXAMPLE 65

Preparation of [6-(n-butylsulfonoyl)-2-[4-(n-butylsulfonoyl)phenyl]benzo[b]thien-3-yl][4-[2-(1-pyrrolidinyl)ethoxy]phenyl]methanone 1.5 g of [6-hydroxy-2-[4-hydroxyphenyl]benzo[b]thien-3-yl][4-[2-(1-pyrrolidinyl)ethoxy]-phenyl]methanone hydrochloride (3 mmol) was suspended in 200 ml of tetrahydrofuran. 1.5 g of triethylamine (15 mmol) and 10 mg of 4-N,N-dimethylaminopyridine were added. The reaction mixture was stirred for several minutes under a nitrogen atmosphere. 1.56 g of n-butylsulfonyl chloride (10 mmol) was dissolved in 50 ml of tetrahydrofuran and slowly added to the reaction mixture over a twenty minute period. The reaction mixture was stirred for eighteen hours at room temperature and under a nitrogen atmosphere. The reaction mixture was evaporated to a gum in vacuo. The crude product was suspended in 100 ml of ethyl acetate and washed with sodium bicarbonate solution and subsequently with water. The organic layer was dried by filteration through anhydrous sodium sulfate and evaporated to a yellow oil. The final product was crystallized from hot ethyl acetate-hexane to afford 410 mg of the title compound.

NMR was consistent with the proposed structure; MS: m/e=700 (M+1) FD;

| Elemental Analysis: | C | H | N |
|---|---|---|---|
| Calculated: | 60.20 | 5.86 | 2.01 |
| Found: | 59.94 | 5.94 | 2.00 |

MW=699; $C_{35}H_{41}NO_8S$.

EXAMPLE 66

Preparation of [6-(n-butylsulfonoyl)-2-[4-(n-butylsulfonoyl)-phenyl]benzo[b]thien-3-yl]-[4-[2-(1-pyrrolidinyl)ethoxy]-phenyl]methanone hydrochloride 350 mg of [6-(n-Butylsulfonoyl)-2-[4-Butylsulfonoyl)-phenyl]benzo[b]thien-3-yl]-[4-[2-(1-pyrrolidinyl)ethoxy]-phenyl]methanone (0.5 mmol) was dissolved in 10 ml of ethyl acetate and a saturated solution of hydrogen chloride in ether was added. No precipitate formed and the reaction mixture was evaporated to a gummy, white solid. The product was triturated with diethyl ether (2×) and filtered and dried in vacuo at room temperature to afford 220 mg of the title compound.

NMR: consistent with the proposed structure;

| Elemental Analysis: | C | H | N |
|---|---|---|---|
| Calculated | 57.09 | 5.75 | 1.90; |
| Found: | 57.27 | 5.91 | 1.86 |

MW=736.37; $C_{35}H_{41}NO_8S_3$—HCl.

EXAMPLE 67

Preparation of [6-hydroxy-2-[4-(n-butylsulfonoyl)-phenyl]benzo[b]-thien-3-yl]-[4-[2-(1-piperidinyl)-ethoxy]phenyl]methanone

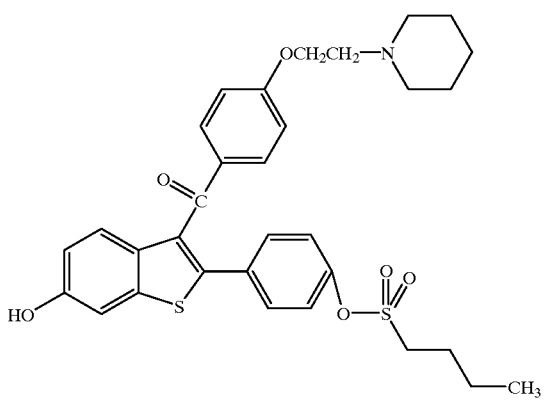

20 g of [6-hydroxy-2-[4-hydroxyphenyl]benzo[b]thien-3-yl]-[4-[2-(1-piperidinyl)ethoxy]phenyl]methanone (Raloxifene) hydrochloride (0.04 mol) was suspended in 250 ml of tetrahydrofuran. Ten grams of triethylamine (0.1 mol) and 10 mg of 4-N,N-dimethylaminopyridine were added. The reaction mixture was stirred for several minutes under nitrogen. 6.25 g of n-butylsulfonylchloride (0.04 mol) was dissolved in 25 ml of tetrahydrofuran and slowly added to the reaction mixture over a period of twenty minutes. The reaction was allowed to continue for 5 days at room temperature and under nitrogen atmosphere. The reaction mixture was evaporated to a gum and suspended in ethyl acetate. The ethyl acetate mixture was washed successively with water, dilute sodium bicarbonate, and water. The ethyl acetate solution was dried by filteration through anhydrous sodium sulfate and evaporated to an amorphous solid.

The resulting solid was dissolved in 50 ml of methylene chloride and chromatographed (HPLC) on a silica gel column eluted with a linear gradient of chloroform to chloroform-methanol (19:1)(v/v). Four fractions were determined by thin layer chromatography and evaporated in vacuo to amorphous solids:

Fraction A: [6-(n-Butylsulfonoyl)-2-[4-(n-butylsulfonoyl)phenyl]benzo[b]thien- 3-yl][4-[2-(1-piperidinyl)ethoxy]phenyl]methanone, 5.43 g Fraction B: [6-hydroxy-2-[4-(n-butylsulfonoyl)-phenyl]benzo[b]-thien-3-yl]-[4-[2-(1-piperidinyl)ethoxy]phenyl]methanone, 2.19 g,
Rf=0.50, silica gel, CHCl₃—MeOH (19:1)v/v Fraction C: [6-(n-butylsulfonoyl)-2-(4-hydroxyphenyl)benzo[b]thien-3-yl]-[4-[2-(1-piperidinyl)ethoxy]phenyl]methanone, 3.60 g Rf=0.41, silica gel, CHCl₃—MeOH (19:1)v/v Fraction D: Raloxifene, 3.94 g All of Fraction B was dissolved in hot ethyl acetate and hexane was added and the title compound crystallized out to afford 1.89 g of the title compound.

NMR: consistent with proposed structure; MS: m/e=594 (M+1) FD;

| Elemental Analysis: | C | H | N |
|---|---|---|---|
| Calculated: | 64.80 | 5.90 | 2.36 |
| Found: | 64.85 | 6.07 | 2.49 |

$C_{32}H_{35}NO_6S_2$.

EXAMPLE 68

Preparation of [6-hydroxy-2-[4-(n-butylsulfonoyl)-phenyl]benzo[b]thien-3-yl]-[4-[2-(1-piperidinyl)ethoxy]phenyl]methanone hydrochloride 1.7 g of [6-hydroxy-2-[4-(n-butylsulfonoyl)-phenyl]benzo[b]-thien-3-yl]-[4-[2-(1-piperidinyl)ethoxy]phenyl]methanone (2.86 mmol) was dissolved in ethyl acetate and a saturated solution of hydrogen chloride-diethyl ether was added. A thick white precipitate formed. The liquid was decanted off. The remaining solid was triturated with diethyl ether (2x) and dried to afford 1.57 g of the title compound as a white amorphous powder.

NMR: consistent with the proposed structure.

| Elemental Analysis: | C | H | N |
|---|---|---|---|
| Calculated: | 60.99 | 5.76 | 2.22; |
| Found: | 61.17 | 5.88 | 2.27 |

MW=630.23; $C_{32}H_{35}NO_6S_2$—HCl; MS: m/e=594 (M—HCl)F.D.

EXAMPLE 69

Preparation of [6-n-butylsulfonoyl-2-[4-hydroxyphenyl]benzo[b]thien-3-yl]-[4-[2-(1-piperidinyl)ethoxy]phenyl]methanone

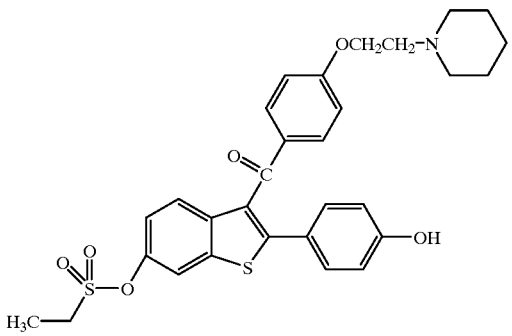

All of fraction C from Example 67 was dissolved in 50 ml of hot ethyl acetate and hexane. No crystallization occurred The solvents were evaporated in vacuo to afford 3.17 g of the title compound as oily, white solid.

NMR: consistent with the proposed structure. MS: m/e= 594 (M+1) FD;

| Elemental Analysis: | C | H | N |
|---|---|---|---|
| Calculated: | 64.84 | 5.90 | 2.36. |
| Found: | 64.37 | 5.87 | 2.28. |

MW=593; $C_{32}H_{35}NO_6S$.

EXAMPLE 70

Preparation of [6-n-butylsulfonoyl-2-[4-hydroxyphenyl]benzo[b]thien-3-yl]-[4-[2-(1-piperidinyl)ethoxy]phenyl]methanone hydrochloride 3 g of [6-n-butylsulfonoyl-2-[4-hydroxyphenyl]-benzo[b]thien-3-yl]-[4-[2-(1-piperidinyl)ethoxy]-phenyl]methanone was dissolved in 50 ml of ethyl acetate and a solution of diethyl ether saturated with hydrogen chloride was added. A thick white precipitate formed and the liquid was decanted off. The solid was triturated (2×) with diethyl ether and dried. This afforded 2.51 g of the title compound as a white amorphous powder.

NMR: consistent with the proposed structure.

| Elemental Analysis: | C | H | N |
|---|---|---|---|
| Calculated: | 60.99 | 5.76 | 2.22; |
| Found: | 60.71 | 5.34 | 2.21 |

MW=630.23; $C_{32}H_{35}NO_6S_2$—HCl; MS: m/e=594 (M—HCl) F.D.

EXAMPLE 71

Preparation of [6-[N-(4-chlorophenyl)carbamoyl]-2-[4-[N-(4-chlorophenyl)carbamoyl]phenyl]benzo[b]thien-3-yl][4-[2-(1-piperidinyl)ethoxy]phenyl]methanone 5.56 g (10.7 mmol) of [6-hydroxy-2-(4-hydroxyphenyl)benzo[b]thien-3-yl]-[4-[2-(1-piperidinyl)ethoxy]phenyl]methanone was dissolved in 200 ml of dry tetrahydrofuran and 5.45 g (35.2 mmol) of 4-chlorophenyl isocynate was added. The reaction mixture was stirred at room temperature under an atmosphere of nitrogen. After 18 hours, the solvent was removed by evaporation in vacuo, and redissolved in chloroform. The chloroform solution was cooled to −20° C. for 24 hours and the precipitate formed was filtered off. The remaining solution was chromatographed (Waters Prep 500, HPLC) on a silica gel column, eluted with a linear gradient of chloroform ending with chloroform-methanol (19:1)(v/v). The desired fractions were determined by thin layer chromatography, combined and evaporated to dryness to afford 4.01 g of the title compound as a tan amorphous powder.

$C_{42}C_{35}Cl_2N_3O_6S$;

| Elemental Analysis: | C | H | N |
|---|---|---|---|
| Calculated: | 64.64 | 4.48 | 5.38 |
| Found: | 65.69 | 4.81 | 4.83 |

MS (FD) m/e=779,781.

EXAMPLE 72

Preparation of [6-[N-(4-chlorophenyl)carbamoyl]-2-[4-[N-(4-chlorophenyl)carbamoyl]phenyl]benzo[b]thien-3-yl][4-[2-(1-piperidinyl)ethoxy]phenyl] methanone hydrochloride 4.01 g of [6-[N-(4-Chlorophenyl)carbamoyl]-2-[4-[N-(4-chlorophenyl)carbamoyl]phenyl]benzo[b]thien-3-yl][4-[2-(1-piperidinyl)ethoxy]-phenyl]methanone was dissolved in 200 ml of ether and a small amount of tetrahydrofuran added to affect solution. A solution of ether, which had been saturated with hydrogen chloride, was added until no further precipitate formed. The reaction mixture was evaporated to dryness and triturated with ether several times. An attempt was made to crystalize the salt from hot ethyl acetate and absolute EtOH, which did work. Evaporation of the solvent, afforded 2.58 g of the title compound as a tan amorphous powder.

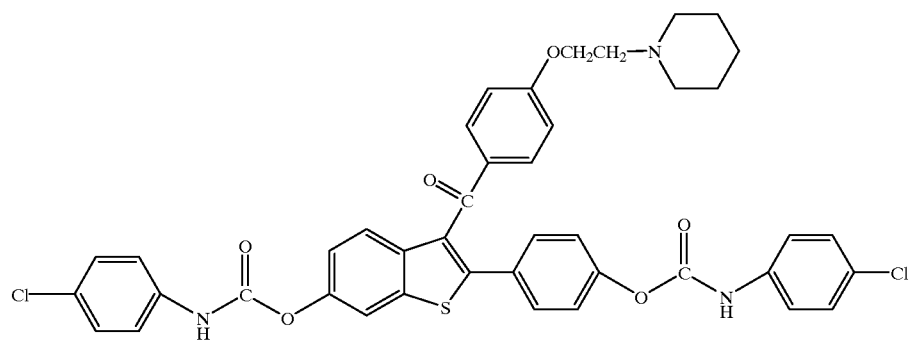

$C_{42}H_{35}Cl_2N_3O_6S$—HCl;

| Elemental Analysis: | C | H | N |
|---|---|---|---|
| Calculated: | 61.73 | 4.44 | 5.14 |
| Found: | 57.43 | 4.29 | 4.19 |

NMR: Consistent with the proposed structure and contains an indeterminate amount of solvent.

EXAMPLE 73

Preparation of [6-(N-(n-butyl)carbamoyl]-2-[4-(N-(n-butyl)carbamoyl)phenyl]benzo[b]thien-3-yl][4-[2-[1-piperidinyl)ethoxylphenyl]methanone

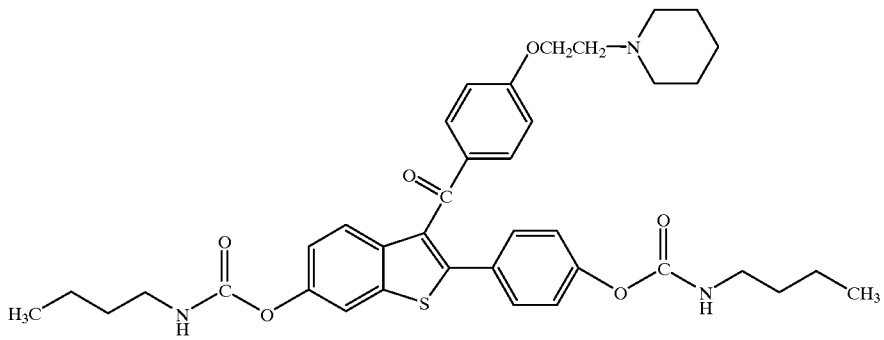

4.47 g (9 mmol) of [6-hydroxy-2-(4-hydroxyphenyl)benzo-[b]thien-3-yl][4-[2-(1-piperidinyl)ethoxy]phenyl]methanone was dissolved in 250 ml of tetrahydrofuran and 4 g (40 mmol) of n-butylisocyanate was added. The reaction mixture, at room temperature and under nitrogen, was allowed to react for 72 hours. The reaction mixture had evaporated by the end of this time and the residue was dissolved in a minimal amount of chloroform. This solution was chromatographed (HPLC) on a silica gel column, eluted with a linear gradient of chloroform to chloroform-methanol (19:1) to afford 4.87 g of the title compound as a tan amorphous powder.

| Elemental Analysis: | C | H | N |
|---|---|---|---|
| Calculated: | 67.73 | 6.75 | 6.52 |
| Found: | 66.43 | 6.67 | 6.24 |

MS (FD) m/e=672 (M+1); NMR was consistent with the proposed structure.

EXAMPLE 74

Preparation of [6-(N-methylcarbamoyl)-2-[4-(N-methylcarbamoyl)phenyl]benzo[b]thien-3-yl][4-[2-(1-piperidinyl)ethoxy]phenyl]methanone

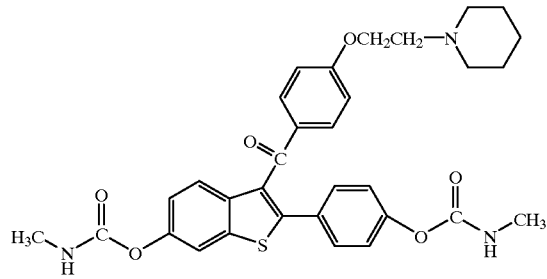

A suspension of 3 g (5.9 mmol) of [6-hydroxy-2(4-hydroxyphenyl)]benzo[b]thien-3-yl][4-[2-(1-piperidinyl)ethoxy]phenyl]methanone hydrochloride in 250 ml of anhydrous tetrahydrofuran was prepared. To this suspension was added 2 g (10 mmol) of triethylamine and the reaction mixture was stirred at room temperature for approximately 15 minutes under a nitrogen atmosphere. To the stirring mixture was added 5.8 g (20 mmol) of methylisocyanate. The reaction was allowed to continue for 36 hours. The reaction mixture was filtered and evaporated to dryness in vacuo. The residue was dissolved in 30 ml of chloroform and chromatographed (HPLC) on a silica gel column, eluted with a linear gradient of solvent of chloroform to chloroform-methanol (19:1). The fractions were analyzed by thin layer chromatography and the desired fractions were combined and evaporated to dryness in vacuo to afford 2.2 g of the title compound as an amorphous powder.

NMR: Consistent with the proposed structure. IR: 3465, 2942, 1741 cm-1 (CHCl$_3$); MS: m/e=588 (M+1) FD; C$_{32}$H$_{33}$N$_3$O$_6$S.

EXAMPLE 75

Preparation of [6-(N-methylcarbamoyl)-2[4-(N-methylcarbamoyl)-phenyl]benzo[b]thien-3-yl][4-[2-(1-piperidinyl)ethoxy]phenyl]methanone Hydrochloride Two grams of the compound of [6-(N-Methylcarbamoyl)-2-[4-(N-methylcarbamoyl)-phenyl]benzo[b]thien-3-yl][4-[2-(1-piperidinyl)ethoxy]phenyl]methanone was disolved in 20 ml of ethyl acetate and a solution of hydrochloric acid-ether was added, forming a white precipitate. The reaction mixture was evaporated to dryness in vacuo. The solids were crystallized from acetone-ethyl acetate, filtered and washed with ethyl acetate and dried to afford 1.98 g of the title compound.

NMR: Consistent with the desired structure.

| Elemental Analysis: | C | H | N |
|---|---|---|---|
| Calculated: | 61.58 | 5.49 | 6.73 |
| Found: | 61.25 | 5.96 | 5.97. |

C$_{32}$H$_{34}$ClN$_3$O$_6$S.

EXAMPLE 76

Preparation of [6-(N-ethylcarbamoyl)-2-[4-(N-ethylcarbamoyl)phenyl]benzo[b]thien-3-yl][4-[2-(1-piperidinyl)ethoxy]phenyl]methanone

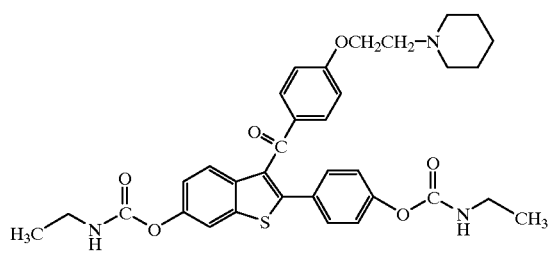

4 g (7.85 mmol) of [6-hydroxy-2-(4-hydroxyphenyl)benzo[b]thien-3-yl][4-[2-(1-piperidinyl)ethoxy]phenyl]methanone hydrochloride was suspended in 250 ml of anhydrous tetrahydrofuran and 3 g (30 mmol) of triethylamine was added. The reaction mixture was stirred at room temperature under nitrogen for 15 minutes.

1.67 g (23.5 mmol) of ethylisocyanate was added. After 24 hours, the reaction was checked by thin layer chromatography, and was not complete. An additional 4.5 g of the isocyanate was added. After 96 hours, the reaction mixture was filtered and chromatographed as in Example 74 to afford 4.23 g of the title compound as a white amorphous powder.

NMR: Consistent with the proposed structure. MS: m/e= 616 (M+1) FD; C$_{34}$H$_{37}$N$_3$O$_6$S.

EXAMPLE 77

Preparation of [6-(N-ethylcarbamoyl)-2-[4-(N-ethylcarbamoyl)phenyl]benzo[b]thien-3-yl][4-[2-(1-piperidinyl)ethoxy]phenyl]methanone hydrochloride This compound was prepared by substantially the same procedures of Example 75, to afford 3.58 g of the title compound.

NMR: Consistent with the proposed structure.

| Elemental Analysis: | C | H | N |
|---|---|---|---|
| Calculated: | 62.61 | 5.37 | 6.44; |
| Found | 62.33 | 6.16 | 6.41. |

C$_{34}$H$_{38}$ClN$_3$O$_6$S.

EXAMPLE 78

Preparation of [6-(N-isopropylcarbamoyl)-2[4-(N-isopropylcarbamoyl)phenyl]benzo[b]thien-3-yl][4-[2-(1-piperidinyl)ethoxy]phenyl]methanone

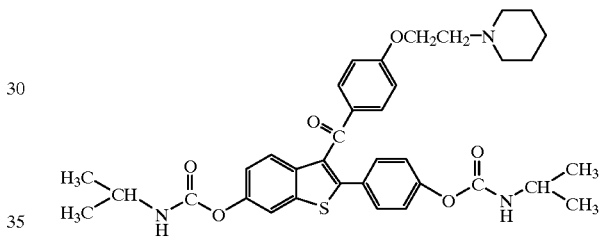

4 g (7.85 mmol) of [6-hydroxy-2-(4-hydroxyphenyl)benzo[b]thien-3-yl][4-[2-(1-piperidinyl)ethoxy]phenyl]methanone hydrochloride was suspended in 250 ml of anhydrous tetrahydrofuran and 3 g (30 mmol) of triethylamine was added. The reaction mixture was stirred for 15 minutes at room temperature and under nitrogen.

2.77 g (32.6 mmol) of isopropylisocyanate was added. After 24 hours, the reaction was checked by thin layer chromatography for completeness and was not complete. An additional 10.8 g (130.4 mmol) of the isocyanate was added and the reaction was allow to continue for another 96 hours. The desired compound was isolated substantially according to the procedures described in Example 19 to afford 4.01 g of the title compound as a tan amorphous powder.

NMR: Consistent with the proposed structure. MS: m/e= 644 (M+1) FD; C$_{36}$H$_{41}$N$_3$O$_6$S.

EXAMPLE 79

Preparation of [6-(N-isopropylcarbamoyl)-2-[4-(N-isopropylcarbamoyl)phenyl]benzo[b]thien-3-yl]-[4-[2-(1-piperidinyl)ethoxy]phenyl]methanone hydrochloride This compound was prepared by substantially following the procedures of Example 75 to afford 3.58 g of the title compound as a white crystalline powder.

NMR: Consistent with the proposed structure.

| Elemental Analysis: | C | H | N |
|---|---|---|---|
| Calculated: | 63.56 | 6.22 | 6.18 |
| Found: | 63.63 | 6.52 | 5.95 |

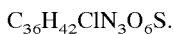

EXAMPLE 80

Preparation of [6-(N-cyclohexylcarbamoyl)-2[4-(N-cyclohexylcarbamoyl)phenyl]benzo[b]thienyl-3-yl][4-[2-(1-piperidinyl)ethoxy]phenyl]methanone

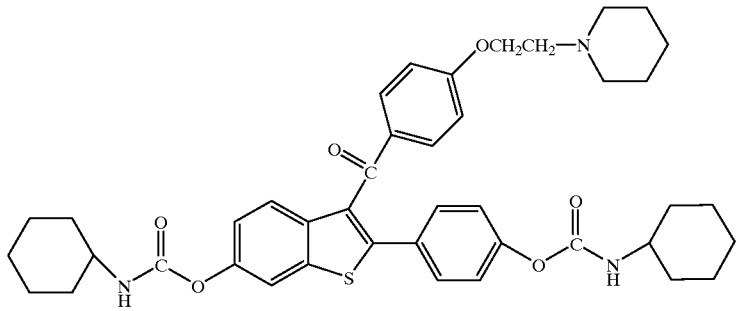

3 g (5.9 mmol) of [6-hydroxy-2-(4-hydroxyphenyl)benzo[b]thien-3-yl][4-[2-(1-piperidinyl)ethoxy]phenyl]methanone hydrochloride was suspended in 250 ml of anhydrous tetrahydrofuran and 2 g (20 mmol) of triethylamine was added. The reaction mixture was stirred for 15 minutes at room temperature under nitrogen. 14.5 g (105 mmol) of cyclohexylisocyanate was added. The reaction was allowed to continue for 48 hours, then an additional 20 mmol of the isocyanate was added. After a further 24 hours, the desired product was isolated substantially according to the procedures of Example 19 to afford 4.07 g of the the title compound as a tan amorphous powder.

NMR: Consistent with the proposed structure. MS: m/e= 724 (M+1) FD; $C_{42}H_{49}N_3O_6S$.

EXAMPLE 81

Preparation of 6-(N-cyclohexylcarbamoyl)-2[4-(N-cyclohexylcarbamoyl)phenyl]benzo[b]thienyl-3-yl][4-[2-(1-piperidinyl)ethoxy]phenyl]methanone Hydrochloride 3.9 g of 6-(N-cyclohexylcarbamoyl)-2[4-(N-cyclohexylcarbamoyl)phenyl]benzo[b]thienyl-3-yl][4-[2-(1-piperidinyl)ethoxy]phenyl]methanone was converted to its hydrochloride salt by substantially the same procedures as described for Example 75 and crystallized from hot ethyl acetate. This afforded 3 g of the title compound as a white powder.

NMR: Consistent with the proposed structure.

| Elemental Analysis: | C | H | N |
|---|---|---|---|
| Calculated: | 66.34 | 6.63 | 5.53 |
| Found: | 66.32 | 6.92 | 5.62 |

EXAMPLE 82

Preparation of [6-(N-phenylcarbamoyl)-2[4-(N-phenylcarbamoyl)phenyl]benzo[b]thien-3-yl][4-[2-(1-piperidinyl)ethoxy]phenyl]methanone

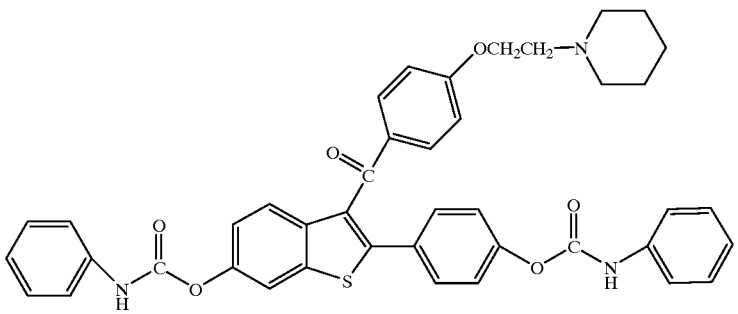

3 g (5.9 mmol) of [6-hydroxy-[2-(4-hydroxyphenyl)benzo[b]thien-3-yl][4-[2-(1-piperidinyl)ethoxy]phenyl]methanone hydrochloride was suspended in 250 ml of anhydrous tetrahydrofuran and 2 g (20 mmol) of triethylamine was added. The reaction mixture was stirred for 15 minutes at room temperature under nitrogen. 15 ml of phenylisocyanate was added and the reaction was allow to continue for 96 hours. An additional 5 ml of isocyanate was added. After a further 48 hours, the reaction mixture was filtered and evaporated to an oil, The oil was triturated with heptane and the liquid decanted off. The oil was dissolved in chloroform and chromatographed (HPLC) on a silica gel column, eluted with a linear gradient of chloroform to chloroform-methanol (19:1). The desired fractions were combined and evaporated to an oil to afford 3.31 g of the title compound.

NMR: Consistent with the proposed structure. MS: m/e= 711 and some 212 (diphenylurea); $C_{42}H_{37}N_3O_6S$.

EXAMPLE 83

Preparation of [6-(N-phenylcarbamoyl)-2-[4-(N-phenylcarbamoyl)phenyl]benzo[b]thien-3-yl][4-[2-(1-piperidinyl)ethoxy]phenyl]methanone Hydrochloride 3.2 g of [6-(N-phenylcarbamoyl)-2[4-(N-phenylcarbamoyl)phenyl]benzo[b]thien-3-yl][4-[2-(1-piperidinyl)ethoxy]phenyl]methanone was disolved in ethyl acetate and filtered. Hydrogen chloride-ether was added to the solution and a white precipitate formed. The liquid was decanted off. The solid was dissolved in a small amount of acetone and filtered, then it is was evaporated to dryness to afford 270 mg of the title compound as a tan amorphous powder.

| Elemental Analysis: | C | H | N |
|---|---|---|---|
| Calculated: | 67.42 | 5.12 | 5.62 |
| Found | 67.51 | 5.37 | 5.50 |

$C_{42}H_{38}ClN_3O_6S$.

EXAMPLE 84

Preparation of [6-methylsulfonoyl-2-[4-methylsulfonoyl)phenyl]benzo[b]-thien-3-yl]-[4-[2-(1-piperidinyl)ethoxy]phenyl]methanone

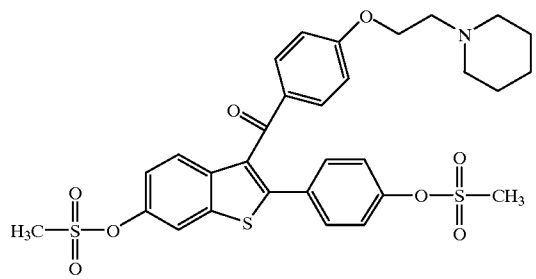

This compound was prepared using the procedure described in *J. Med. Chem.* 27:1057 (1984), by Jones, C. D., Jevnikar, M. G., Pike, A. J., Peters, M. K., Black, L. J., Thompson, A. R., Falcone, J. F., and Clemens, J. A. Antiestrogens. 2.: Structure-Activity Studies in a Series of 3-Aroyl-2-arylbenzo[b]thiophene Derivatives Leading to [6-Hydroxy-2-(4-hydroxyphenyl)benzo[b]thien-3-yl][4-[2-(1-piperidinyl)ethoxy]phenyl]methanone Hydrochloride (LY156758), a Remarkably Effective Estrogen Antagonist with Only Minimal Intrinsic Estrogenicity.

EXAMPLE 85

Preparation of [6-n-propylsulfonoyl-2-[4-n-propylsulfonoyl)phenyl]benzo[b]-thien-3-yl]-[4-[2-(1-piperidinyl)ethoxy]phenyl]methanone

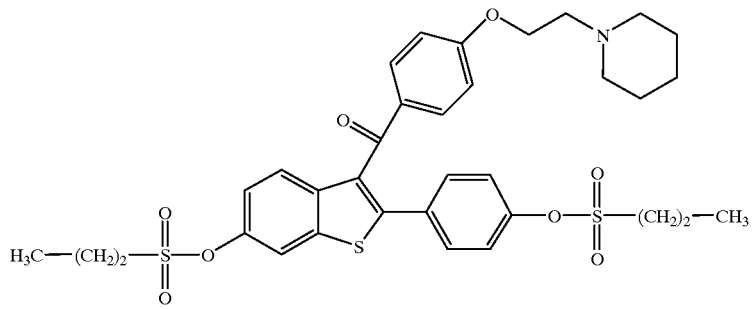

This compound was prepared using the procedure described in U.S. Pat. No. 5,482,949, Jan. 9, 1996, Sulfonate Derivatives of 3-Aroylbenzo[b]thiophenes, by Black, L. J., Bryant, H. U., and Cullinan, G. J.

By substantially following the procedures described above one skilled in the art can prepare the other compounds of Formula I.

The current invention concerns the discovery that a select group of heterocyclic compounds, those of Formula I, are useful for treating resistant neoplasms. The methods of treatment provided by this invention are practiced by administering to a human or other mammal in need thereof a multidrug resistance reversing amount of a compound of Formula I or a pharmaceutically acceptable salt or solvate thereof, that is effective to make the neoplasms less resistant to chemotherapy. In making the neoplasm less resistant, the compounds of the invention may be used on neoplasms having intrinsic and/or acquired resistance. Such neoplasms include those which have a pathway for resistance which includes the protein p190. Resistance to drugs such as epipodophyllotoxins and anthracyclines are linked to p190. The treatment of the resistant and susceptible neoplasm will result in a reversal or inhibition of resistance, or in other words, will cause the neoplasm to be more sensitive to the appropriate chemotherapy such as treatment with vinblastine, vincristine, vindesine, navelbine, daunorubicin, doxorubicin, mitroxantrone, etoposide, teniposide, mitomycin C, actinomycin D, taxol, topotecan, mithramycin, colchicine, puromycin, podophyllotoxin, ethidium bromide, emetine, gramicidin D, and valinomycin.

The compounds of the invention may be used for many resistant neoplasms, including colon cancer, mesothelioma, melanoma, prostate cancer, ovarian cancer, non-small cell lung cancer, small-cell lung cancer, bladder cancer, endometrial cancer, leukemia, renal cancer, liver cancer, neurological tumors, testicular cancer, breast cancer, and large cell lymphoma. More particular types of cancer are Hodgkin's disease, Karposi's sarcoma, and acute granulocytic leukemia.

The biological activity of the compounds of the present invention was evaluated employing an initial screening assay which rapidly and accurately measured the activity of the tested compound in reversing the resistance present in a multidrug resistant tumor. Assays useful for evaluating this reversing capability are well known in the art. See, e.g., T. McGrath, et al., *Biochemical Pharmacology*, 38:3611, (1989); D. Marquardt and M. S. Center, *Cancer Research*, 52:3157, (1992); and D. Marquardt, et al., *Cancer Research*, 50:1426, (1990).

Assay for Reversal of p190-Mediated Doxorubicin Resistance

HL60/ADR is a continuous cell line, which was selected for ADRIAMYCIN™ resistance by culturing HL60, a human acute myeloblastic leukemia cell line, in increasing concentrations of ADRIAMYCIN™ until a highly resistant variant was attained.

HL60/ADR cells were grown in RPMI 1640 (Gibco) containing 10% fetal bovine serum (FBS) and 250 µg/ml GENTAMICIN™ (Sigma). Cells were harvested; washed twice with assay medium (same as culture media); counted; and diluted to $2\times10^5$ cells/ml in assay medium. Fifty microliters of cells were aliquoted into wells of a 96 well tissue culture plate. One column of each 96 well plate served as a negative control and received assay medium containing no cells.

Test compounds and references compounds were dissolved in dimethyl sulfoxide (DMSO) at a concentration of 5 mM. Samples were diluted to 20 µM in assay medium and 25 µl of each test compound was added to 6 wells. Assay standards were run in quadruplicate. Twenty-five microliters of 0.4% DMSO was added to four wells as a solvent control. Assay media was added to all wells to achieve a final volume of 100 µl per well.

The plates were incubated at 37° C. for 72 hours in a humidified incubator with a 5% carbon dioxide atmosphere. Cell viability and vitality was measured by oxidation of a tetrazolium salt suing standard conditions. The plates were incubated for 3 hours at 37° C. Absorbance was determined at 490 nm using a microtitre plate reader.

The ability of a test compound to reverse the resistance of HL60/ADR cells to an oncolytic was determined by comparison of the absorbance of the wells containing a test compound in addition to the oncolytic (such as ADRIAMYCIN™) with the absorbance of wells containing the oncolytic without a test compound. Controls were used to eliminate background and to ensure the results were not artifactual. The results of the assay are expressed as percent inhibition of cell growth. The oncolytic alone at the tested concentration does not usually inhibit the growth of HL60/ADR cells.

Assay for Reversal of P-Glycoprotein-Mediated Doxorubicin Resistance

The human cell leukemia cell lines CCRF-CEM and the multidrug resistant CEM/VLB100 [selected against 100 ng/ml vinblastine sulfate, as described in W. T. Beck, et al., *Cancer Research*, 39:2070–2076 (1979)] were used to determine the ability of the compounds of the present invention to reverse multidrug resistance mediated by the P-glycoprotein. The cells were maintained in SMEM medium supplemented with 10% fetal bovine serum and 2 mM 1-glutamine in a humidified incubator with 5% added carbon dioxide. Cell numbers were determined suing a Coulter Counter model ZM™. Cells were subcultured every 3–4 days.

Cell viability was determined using a modified MTT [3-(4,5-dimethylthiazol-2-yl)-2,5-diphenyltetrazolium bromide] dye reduction methods. See, F. Denziot and R. Lang, *Journal of Immunological Methods*, 89:271–277 (1986). Cells were harvested during the logarithmic growth phase, and seeded in 96-well seroculture plates at $7.5\times10^3$ cells/well and cultured for 72 hours in the presence of serially diluted oncolytics. The oncolytics employed were vinblastine sulfate, ADRIAMYCIN™, ETOPOSIDE™, and taxol. These compounds were used with and without the compounds of the present invention.

Initial leads were discovered by a single well assay using a fixed concentration of vinblastine sulfate (4 ng/ml) and modulator (5 µM). The cytotoxicity of the modulator of the present invention alone was also determined. Modulators were prepared as 2 mM stocks in dimethylsulfoxide and added to the wells to give a final concentration ranging from 5 µM to 0.5 µM. After 72 hours, 20 µl of freshly prepared MTT (5 mg/ml in Dulbecco's phosphate buffered saline, pH 7.5) was added to each well and placed for four hours in a 37° C. incubator.

Cells were pelleted and 70 µl of cell pellet was carefully removed from each well. To this cell pellet were added 100

μl of 2-propanol/0.04 N hydrochloric acid to dissolve the blue formazan-stained cells. Cells were resuspended 5–10 times with a multipipettor or until no particulate matter was visible. The plates were then immediately read with a microplate reader at a wavelength of 570 nm and a reference wavelength of 630 nm. The controls were measured in quadruplicate and those containing modulator were measured in duplicate.

The amount of drug, modulator, or drug and modulator that inhibited fifty percent of the growth of the cells ($IC_{50}$) was calculated from semilog dose response curves in the presence and absence of modulators for both the parent and the resistant cell lines. The fold shift was calculated as the $IC_{50}$ for cells treated with oncolytic alone divided by the $IC_{50}$ for cells treated with oncolytic and modulator.

The compounds of Formula I demonstrated a significant effect in reversing the P-190 and P-glycoprotein mediated multiple drug resistances. Many of the compounds showed very significant enhancement of activity in combination with the oncolytic agent as opposed to the oncolytic agent alone.

The compounds of Formula I are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

The present invention also includes methods employing pharmaceutical compositions which contain, as the active ingredient, the compounds of Formula I associated with pharmaceutically acceptable carriers. In making the compositions of the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage form" refers to physically discrete units suitable as unitary dosages dosages for human subjects and other mammals, each unit containing a predetermined quantity of active material calculated to produce the desired therapeutic effect, in association with a suitable pharmaceutical excipient.

The active compound is effective over a wide dosage range. For examples, dosages per day normally fall within the range of about 0.5 to about 30 mg/kg of body weight. In the treatment of adult humans, the range of about 1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

For preparing solid compositions such as tablets the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face mask, tent, or intermittent positive pressure breathing machine. Solution, suspension, or powder compositions may be administered, preferably orally or nasally, from devices which deliver the formulation in an appropriate manner.

The following formulation examples are illustrative only and are not intended to limit the scope of the invention in any way. "Active ingredient," of course, means a compound according to Formula I or a pharmaceutically acceptable salt or solvate thereof.

Formulation Example 1

Hard gelatin capsules containing the following ingredients are prepared:

| Ingredient | Quantity (mg/capsule) |
|---|---|
| Active Ingredient (s) | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
|---|---|
| Active Ingredient (s) | 30.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Active Ingredient (s) | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
|---|---|
| Active Ingredient (s) | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
|---|---|
| Active Ingredient (s) | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
| --- | --- |
| Active Ingredient (s) | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
| --- | --- |
| Active Ingredient (s) | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules, each containing 15 mg of medicament, are made as follows:

| Ingredient | Quantity (mg/capsule) |
| --- | --- |
| Active Ingredient (s) | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Example 9

An intravenous formulation may be prepared as follows:

| Ingredient | Quantity |
| --- | --- |
| Active Ingredient (s) | 250.0 mg |
| Isotonic saline | 1000 ml |

Formulation Example 10

A topical formulation may be prepared as follows:

| Ingredient | Quantity |
| --- | --- |
| Active Ingredient (s) | 1–10 g |
| Emulsifying Wax | 30 g |
| Liquid Paraffin | 20 g |
| White Soft Paraffin | to 100 g |

The white soft paraffin is heated until molten. The liquid praffin and emulsifying wax are incorporated and stirred until dissolved. The active ingredient is added and stirring is continued until dispersed. The mixture is then cooled until solid.

Formulation Example 11

Sublingual or buccal tablets, each containing 10 mg of active ingredient, may be prepared as follows:

| Ingredient | Quantity Per Tablet |
| --- | --- |
| Active Ingredient (s) | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

We claim:

1. A method of treating a susceptible neoplasm having intrinsic and/or acquired multidrug resistance in a mammal which comprises administering to a mammal in need thereof an enhanced multidrug resistance reversing amount of a compound having the formula

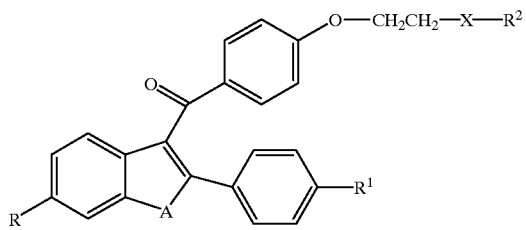

wherein:

A is —O—, —S(O)$_m$—, —N(R$^{11}$)—, —CH$_2$CH$_2$—, or —CH=CH—;

m is 0, 1, or 2;

R$^{11}$ is H, or C$_1$–C$_6$ alkyl;

X is a bond or C$_1$–C$_4$ alkylidenyl;

R$^2$ is a group of the formula

wherein R$^4$ and R$^5$ are independently C$_1$–C$_6$ alkyl or combine to form, along with the nitrogen to which they are attached, a heterocyclic ring selected from the group consisting of hexamethyleneiminyl, piperazino, heptamethyleneiminyl, 4-methylpiperidinyl, imidazolinyl, piperidinyl, pyrrolidinyl, or morpholinyl;

R is hydroxy, halo, hydrogen, C$_3$–C$_8$ cycloalkyl, C$_2$–C$_7$ alkanoyloxy, C$_1$–C$_6$ alkoxy, —OSO$_2$—(C$_1$–C$_{10}$ alkyl),

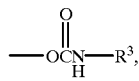

or phenyl, said phenyl being optionally substituted with one, two, or three moieties selected from the group consisting of C$_1$–C$_4$ alkyl, C$_1$–C$_4$ alkoxy, nitro, chloro, or fluoro;

R$^1$ is hydroxy, halo, hydrogen, C$_3$–C$_8$ cycloalkyl, C$_2$–C$_7$ alkanoyloxy, C$_1$–C$_6$ alkoxy, —OSO$_2$—(C$_1$–C$_{10}$ alkyl)

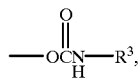

or phenyl, said phenyl being optionally substituted with one, two, or three moieties selected from the group consisting of C$_1$–C$_4$ alkyl, C$_1$–C$_4$ alkoxy, nitro, chloro, or fluoro;

each R$^3$ is independently C$_1$–C$_6$ alkyl, C$_3$–C$_8$ cycloalkyl, unsubstituted or substituted phenyl where the substituent is halo, C$_1$–C$_6$ alkyl or C$_1$–C$_6$ alkoxy;

with the proviso that when X is a bond and A is —S—, R and R$^1$ are not both selected from the group consisting of hydroxy, methoxy, and C$_2$–C$_7$ alkanoyloxy;

or a pharmaceutically acceptable salt or solvate thereof, in combination with an effective amount of one or more oncolytic agents selected from the group of anthracyclins, vinca alkaloids and/or epipodophyllotoxins.

2. A method as claimed in claim 1 employing a compound wherein X is a bond or methylene, or a pharmaceutically acceptable salt or solvate thereof.

3. A method as claimed in claim 2 employing a compound wherein R$^2$ is hexamethyleneiminyl, piperidinyl, or pyrrolidinyl, or a pharmaceutically acceptable salt or solvate thereof.

4. A method as claimed in claim 3 employing a compound wherein A is —S(O)$_m$—, m is 0, 1, or 2; or a pharmaceutically acceptable salt or solvate thereof.

5. A method as claimed in claim 4 employing a compound wherein at least one of R and R$^1$ is —OSO$_2$—(C$_1$–C$_{10}$ alkyl) or

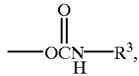

or a pharmaceutically acceptable salt or solvate thereof.

6. A method as claimed in claim 5 employing a compound selected from the group consisting of [6-(n-butylsulfonoyl)-2-[4-(n-butylsulfonoyl)phenyl]benzo[b]thien-3-yl][4-[2-(1-piperidinyl)ethoxy]-phenyl]methanone, [6-(n-pentylsulfonoyl)-2-[4-(n-pentylsulfonoyl)phenyl]benzo[b]thien-3-yl][4-[2-(1-piperidinyl)ethoxy]-phenyl]methanone, [6-(n-hexylsulfonoyl)-2-[4-(n-hexylsulfonoyl)phenyl]benzo[b]thien-3-yl][4-[2-(1-piperidinyl)ethoxy]-phenyl]methanone, [6-(n-butylsulfonoyl)-2-[4-(n-butylsulfonoyl)phenyl]benzo[b]thien-3-yl][4-[3-(1-piperidinyl)propyloxy]phenyl]methanone, [6-(n-butylsulfonoyl)-2-[4-(n-butylsulfonoyl)phenyl]benzo[b]thien-3-yl]-[4-[2-(1- pyrrolidinyl)ethoxy]-phenyl]methanone, [6-hydroxy-2-[4-(n-butylsulfonoyl)-phenyl]benzo[b]-thien-3-yl]-[4-[2-(1-piperidinyl)-ethoxy]phenyl]methanone, [6-n-butylsulfonyl-2-[4-hydroxyphenyl]benzo[b]thien-3-yl]-[4-[2-(1-piperidinyl)ethoxy]phenyl]methanone, [6-[N-(4-chlorophenyl)carbamoyl]-2-[4-[N-(4-chlorophenyl)carbamoyl]phenyl]benzo[b]thien-3-yl][4-[2-(1-piperidinyl)ethoxy]phenyl]methanone, [6-(N-(n-butyl)carbamoyl]-2-[4-[N-(n-butyl)carbamoyl]phenyl]benzo[b]thien-3-yl][4-[2-(1-piperidinyl)ethoxy]phenyl]methanone, [6-(N-methylcarbamoyl)-2-[4-(N-methylcarbamoyl)phenyl]benzo[b]thien-3-yl][4-[2-(1-piperidinyl)ethoxy]phenyl]methanone, [6-(N-ethylcarbamoyl)-2-[4-(N-ethylcarbamoyl)phenyl]benzo[b]thien-3-yl][4-[2-(1-piperidinyl)ethoxy]phenyl]methanone, [6-(N-isopropylcarbamoyl)-2[4-(N-isopropylcarbamoyl)phenyl]benzo[b]thien-3-yl][4-[2-(1-piperidinyl)ethoxy]phenyl]methanone, and [6-(N-cyclohexylcarbamoyl)-2[4-(N-cyclohexylcarbamoyl)phenyl]benzo[b]thienyl-3-yl][4-[2-(1-piperidinyl)ethoxy]phenyl]methanone, or a pharmaceutically acceptable salt or solvate thereof.

7. A method as claimed in claim 1 employing an oncolytic agent selected from the group consisting of vinblastine, vincristine, vindesine, navelbine, daunorubicin, doxorubicin, mitroxantrone, etoposide, teniposide, mitomycin C, actinomycin D, taxol, topotecan, mithramycin, colchicine, puromycin, podophyllotoxin, ethidium bromide, emetine, gramicidin D, and valinomycin.

8. A method as claimed in claim 1 employing an oncolytic agent selected from the group consisting of vinblastine, vincristine, vindesine, navelbine, daunorubicin, doxorubicin, mitroxantrone, etoposide, teniposide, mitomycin C, actinomycin D, taxol, topotecan, mithramycin, colchicine, puromycin, and podophyllotoxin.

9. A method as claimed in claim 1 wherein said susceptible neoplasm is selected from the group consisting of colon cancer, mesothelioma, melanoma, prostate cancer, ovarian cancer, non-small cell lung cancer, small-cell lung cancer, bladder cancer, endometrial cancer, leukemia, testicular cancer, breast cancer, and large cell lymphoma, renal cancer, liver cancer, neurological tumors, Hodgkin's disease, Karposi's sarcoma, and acute granulocytic leukemia.

10. The method of claim 1 in which said compound is

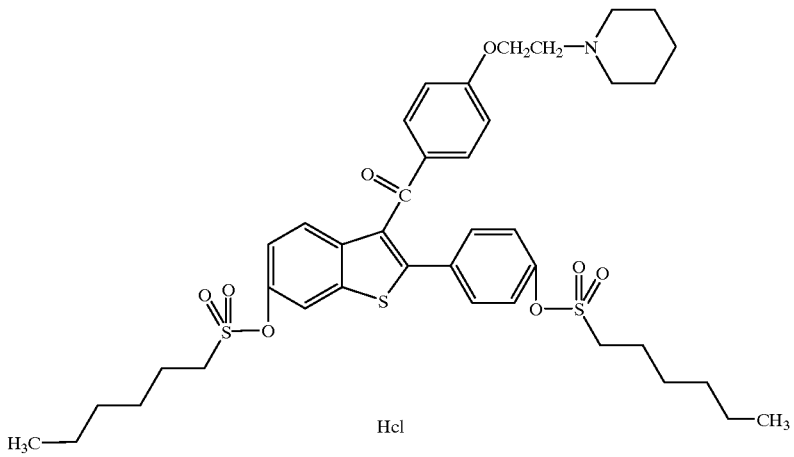

which is named [[6-(N-hexylsulfonoyl)-2-[4-(N-hexylsulfonyl)-phenyl]benzo[b]thien-3-yl][4-[2-(1-piperidinyl)ethoxy-]phenyl]methanone, hydrochloride and in which said oncolytic agent is vinblastine.

11. A pharmaceutical formulation comprising:
(a) an enhanced multidrug resistance reversing amount of a compound of the formula

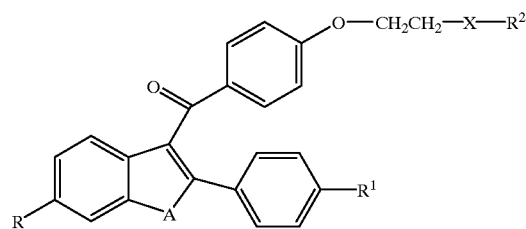

wherein:
A is —O—, —S(O)$_m$—, —N(R$^{11}$)—, —CH$_2$CH$_2$—, or —CH=CH—;
m is 0, 1, or 2;
X is a bond or C$_1$–C$_4$ alkylidenyl;
R$^2$ is a group of the formula

wherein R$^4$ and R$^5$ are independently C$_1$–C$_6$ alkyl or combine to form, along with the nitrogen to which they are attached, a heterocyclic ring selected from the group consisting of hexamethyleneiminyl, piperazino, heptamethyleneiminyl, 4-methylpiperidinyl, imidazolinyl, piperidinyl, pyrrolidinyl, or morpholinyl;
R is hydroxy, halo, hydrogen, C$_3$–C$_8$ cycloalkyl, C$_2$–C$_7$ alkanoyloxy, C$_1$–C$_6$ alkoxy, or phenyl, said phenyl being optionally substituted with one, two, or three moieties selected from the group consisting of $C_1$–$C_4$ alkyl, $C_1$–$C_4$ alkoxy, nitro, chloro, fluoro, trifluoromethyl —$OSO_2$—($C_1$–$C_{10}$ alkyl) or

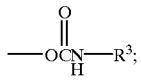

$R^1$ is hydroxy, halo, hydrogen, $C_3$–$C_8$ cycloalkyl, $C_2$–$C_7$ alkanoyloxy, $C_1$–$C_6$ alkoxy, or phenyl, said phenyl being optionally substituted with one, two, or three moieties selected from the group consisting of $C_1$–$C_4$ alkyl, $C_1$–$C_4$ alkoxy, nitro, chloro, fluoro, trifluoromethyl —$OSO_2$—($C_1$–$C_{10}$ alkyl) or

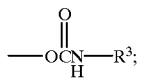

each $R^3$ is independently $C_1$–$C_6$ alkyl, $C_3$–$C_8$ cycloalkyl, unsubstituted or substituted phenyl where the substituent is halo, $C_1$–$C_6$ alkyl or $C_1$–$C_6$ alkoxy;

with the proviso that when X is a bond and A is —S—, R and $R^1$ are not both selected from the group consisting of hydroxy, methoxy, and $C_2$–$C_7$ alkanoyloxy;

or a pharmaceutically acceptable salt or solvate thereof;

(b) an effective amount of one or more oncolytic agents selected from the group of anthracyclins, vinca alkaloids and/or epipodophyllotoxins; and (c) one or more pharmaceutically acceptable carriers, diluents, or excipients therefor.

12. A formulation as claimed in claim 11 employing a compound of (a) wherein X is a bond or methylene, or a pharmaceutically acceptable salt or solvate thereof.

13. A formulation as claimed in claim 12 employing a compound of (a) wherein $R^2$ is hexamethyleneiminyl, piperidinyl, or pyrrolidinyl, or a pharmaceutically acceptable salt or solvate thereof.

14. A formulation as claimed in claim 13 employing a compound of (a) wherein A is —$S(O)_m$—, or a pharmaceutically acceptable salt or solvate thereof.

15. A formulation as claimed in claim 14 employing a compound of (a) wherein at least one of R and $R^1$ is —$OSO_2$—($C_1$–$C_{10}$ alkyl) or

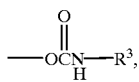

or a pharmaceutically acceptable salt or solvate thereof.

16. A formulation as claimed in claim 15 employing a compound of (a) selected from the group consisting of [6-(n-butylsulfonoyl)-2-[4-(n-butylsulfonoyl)phenyl]benzo[b]thien-3-yl][4-[2-(1-piperidinyl)ethoxy]-phenyl]methanone, [6-(n-pentylsulfonoyl)-2-[4-(n-pentylsulfonoyl)phenyl]benzo[b]thien-3-yl][4-[2-(1-piperidinyl)ethoxy]-phenyl]methanone, [6-(n-hexylsulfonoyl)-2-[4-(n-hexylsulfonoyl)phenyl]benzo[b]thien-3-yl][4-[2-(1-piperidinyl)ethoxy]-phenyl]methanone, [6-(n-butylsulfonoyl)-2-[4-(n-butylsulfonoyl)phenyl]benzo[b]thien-3-yl][4-[3-(1-piperidinyl)propyloxy]phenyl]methanone, [6-(n-butylsulfonoyl)-2-[4-(n-butylsulfonoyl)phenyl]benzo[b]thien-3-yl]-[4-[2-(1-pyrrolidinyl)ethoxy]-phenyl]methanone, [6-hydroxy-2-[4-(n-butylsulfonoyl)-phenyl]benzo[b]-thien-3-yl]-[4-[2-(1-piperidinyl)-ethoxy]phenyl]methanone, [6-n-butylsulfonyl-2-[4-hydroxyphenyl]benzo[b]thien-3-yl]-[4-[2-(1-piperidinyl)ethoxy]phenyl]methanone, [6-[N-(4-chlorophenyl)carbamoyl]-2-[4-[N-(4-chlorophenyl)carbamoyl]phenyl]benzo[b]thien-3-yl][4-[2-(1-piperidinyl)ethoxy]phenyl]methanone, [6-(N-(n-butyl)carbamoyl]-2-[4-[N-(n-butyl)carbamoyl]phenyl]benzo[b]thien-3-yl][4-[2-(1-piperidinyl)ethoxy]phenyl]methanone, [6-(N-methylcarbamoyl)-2-[4-(N-methylcarbamoyl)phenyl]benzo[b]thien-3-yl][4-[2-(1-piperidinyl)ethoxy]phenyl]methanone, [6-(N-ethylcarbamoyl)-2-[4-(N-ethylcarbamoyl)phenyl]benzo[b]thien-3-yl][4-[2-(1-piperidinyl)ethoxy]phenyl]methanone, [6-(N-isopropylcarbamoyl)-2[4-(N-isopropylcarbamoyl)phenyl]benzo[b]thien-3-yl][4-[2-(1-piperidinyl)ethoxy]phenyl]methanone, and [6-(N-cyclohexylcarbamoyl)-2[4-(N-cyclohexylcarbamoyl)phenyl]benzo[b]thienyl-3-yl][4-[2-(1-piperidinyl)ethoxy]phenyl]methanone, or a pharmaceutically acceptable salt or solvate thereof.

17. A formulation as claimed in claim 11 wherein said oncolytic agent is selected from the group consisting of vinblastine, vincristine, vindesine, navelbine, daunorubicin, doxorubicin, mitroxantrone, etoposide, teniposide, mitomycin C, actinomycin D, taxol, topotecan, mithramycin, colchicine, puromycin, podophyllotoxin, ethidium bromide, emetine, gramicidin D, and valinomycin.

* * * * *